US012673098B2

(12) United States Patent
Schreiber et al.

(10) Patent No.: US 12,673,098 B2
(45) Date of Patent: Jul. 7, 2026

(54) METHODS AND COMPOSITIONS FOR TREATING CORONAVIRAL INFECTIONS

(71) Applicant: Yeda Research and Development Co. Ltd., Rehovot (IL)

(72) Inventors: Gideon Schreiber, Rehovot (IL); Jiri Zahradnik, Rehovot (IL); Yinon Rudich, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 604 days.

(21) Appl. No.: 18/122,169

(22) Filed: Mar. 16, 2023

(65) Prior Publication Data

US 2023/0263884 A1     Aug. 24, 2023

Related U.S. Application Data

(63) Continuation of application No. PCT/IL2021/051154, filed on Sep. 22, 2021.

(60) Provisional application No. 63/125,984, filed on Dec. 16, 2020.

(30) Foreign Application Priority Data

Sep. 23, 2020     (IL) .......................................... 277546

(51) Int. Cl.
| | |
|---|---|
| *A61K 39/215* | (2006.01) |
| *C07K 14/005* | (2006.01) |
| *A61K 38/00* | (2006.01) |

(52) U.S. Cl.
CPC .......... *A61K 39/215* (2013.01); *C07K 14/005* (2013.01); *A61K 38/00* (2013.01); *C12N 2770/20022* (2013.01)

(58) Field of Classification Search
None
See application file for complete search history.

(56) References Cited

U.S. PATENT DOCUMENTS

| | | | | |
|---|---|---|---|---|
| 11,382,968 B2 * | 7/2022 | Georges | ................ | C12N 15/86 |
| 2016/0376321 A1 | 12/2016 | Hotez et al. | | |
| 2023/0089695 A1 * | 3/2023 | Chen | ........................ | C12N 7/04 |

FOREIGN PATENT DOCUMENTS

WO      WO 2022/064494      3/2022

OTHER PUBLICATIONS

Zahradnik et al. (Nature Microbiology, 2021, p. 1188-1198).*
International Search Report and the Written Opinion Dated Apr. 22, 2022 From the International Searching Authority Re. Application No. PCT/IL2021/051154. (17 Pages).
Invitation to Pay Additional Fees, Communication Relating to the Results of the Partial International Search and the Provisional Opinion Dated Feb. 22, 2022 From the International Searching Authority Re. Application No. PCT/IL2021/051154. (12 Pages).
Office Action and Search Report Dated May 10, 2021 From the Israel Patent Office Re. Application No. 277546. (8 Pages).
Baig et al. "Identification of a Potential Peptide Inhibitor of SARS-CoV-2 Targeting Its Entry Into the Host Cells", Drugs in R&D, 20(3): 161-169, Published Online Jun. 26, 2020.
Floyd et al. C5a Receptor Oligomerization II. Fluoresnce Resonance Energy Transfer Studies of a Human G Protein-Coupled Recepctor Expressed in Yeast, Journal of Biological Chemistry 278(37):35354-3561, Sep. 12, 2003.
Geneseq "Sars-CoV-2 Spike Protein Receptor Binding Domain (RBD), SEQ 415 ", Database Geneseq [Online], XP002805545, Retrieved from EBI Accession No. GSP:BJV39000, Database Accession No. BJV39000, Oct. 14, 2021.
Huang et al. "Structural and Functional Properties of SARS-CoV-2 Spike Protein: Potential Antivirus Drug Development for COVID-19", Acta Pharmacologica Sinica, 41(9): 1141-1149, Published Online Aug. 3, 2020.
Hussain et al. "Structural Variations in Human ACE2 May Influence Its Binding With SARS-CoV-2 Spike Protein", Journal of Medical Virology, 92(9): 1580-1586, Published Online Apr. 15, 2020.
Starr et al. "Deep Mutational Scanning of SARS-CoV-2 Receptor Binding Domain Reveals Constraints on Folding and ACE2 Binding", Cell, 182(5): 1295-1310, Published Online Aug. 11, 2020.
Struck et al. "A Hexapeptide of the Receptor-Binding Domain of SARS Corona Virus Spike Protein Bocks Viral Entry Into Host Cells via the Human Receptor ACE2", Antiviral Research, 94(3): 288-296, Published Online Jan. 17, 2012.
Uchanski et al. "An Improved Yeast Surface Display Platform for the Screening of Nanobody Immune Libraries", Scientific Reports, 9(1): 382-1-382-12, Published Online Jan. 23, 2019.

* cited by examiner

*Primary Examiner* — Agnieszka Boesen

(57)          ABSTRACT

A polypeptide comprising an amino acid sequence of SARS COV-2 receptor-binding domain (RBD) is disclosed, wherein said amino acid sequence comprises a modification at position 358 and at least two additional modifications at two positions selected from the group consisting of 484, 498 and 501, wherein the polypeptide binds soluble, monomeric angiotensin-converting enzyme 2 (ACE2) receptor. Uses thereof are further disclosed.

19 Claims, 12 Drawing Sheets

Specification includes a Sequence Listing.

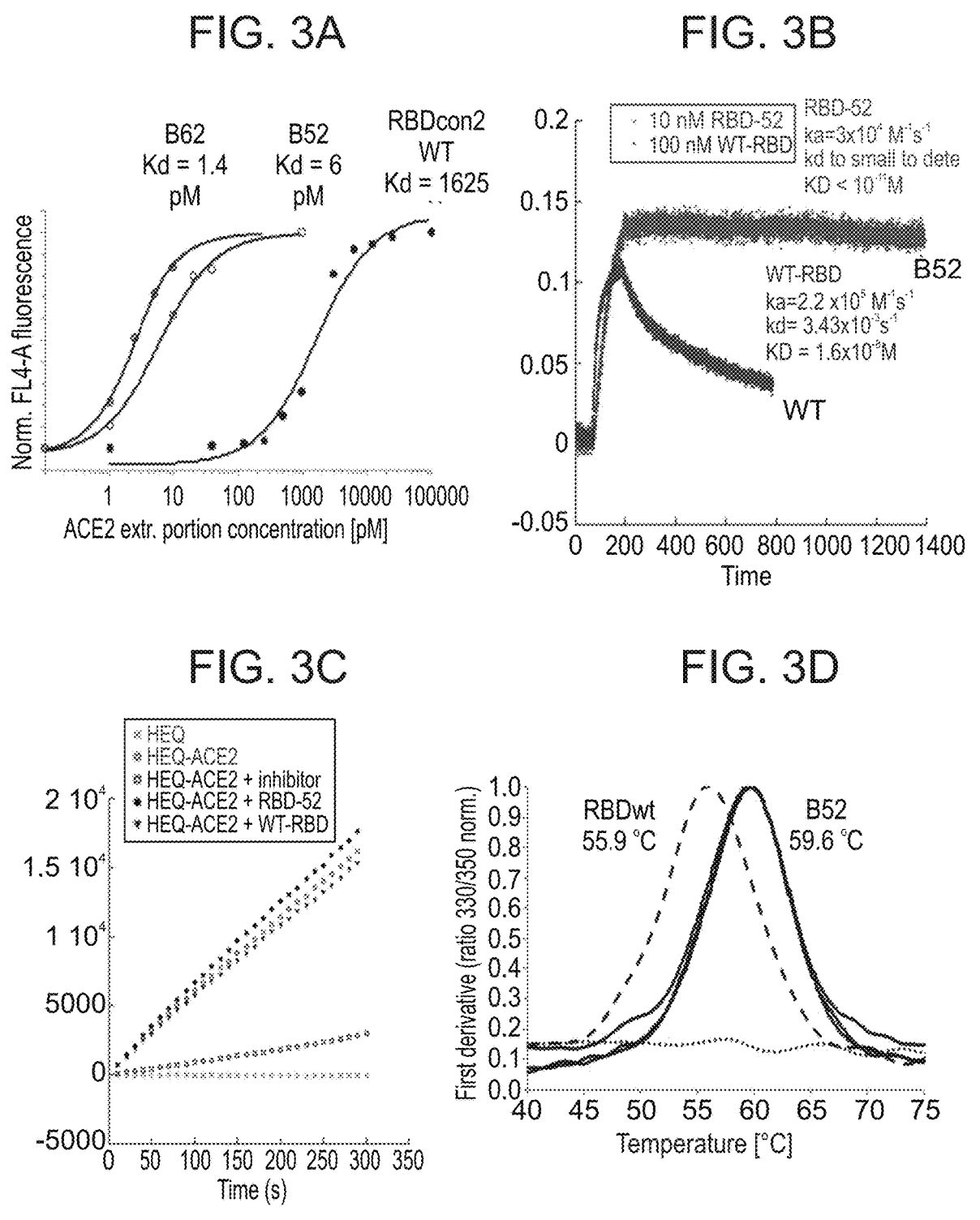

RBDcon2
WT
Kd = 1625

FIG. 3B 10 nM RBD-52
100 nM WT-RBD

RBD-52
ka=3x10⁴ M⁻¹s⁻¹
kd to small to dete
KD < 10⁻¹¹M

WT-RBD
ka=2.2 x10⁵ M⁻¹s⁻¹
kd= 3.43x10⁻³s⁻¹
KD = 1.6x10⁻⁸M

HEQ
HEQ-ACE2
HEQ-ACE2 + inhibitor
HEQ-ACE2 + RBD-52
HEQ-ACE2 + WT-RBD

FIG. 3D

RBDwt
55.9 °C

B52
59.6 °C

○ Stabilization
○ Fast association
● Affinity

I458F
I468T
N460K
T470M
S477N
E484K
V445K
Q498R
N501Y
ACE2

Binding affinity (Biacore S200)

— 160 nM
— 80 nM
— 40 nM
— 20 nM
— 10 nM
— 5 nM

Signal

WT

Time (s)

HEQ
HEQ-ACE2
HEQ-ACE2 + RBD-62

Time (s)

Signal

RBD-62

Time (s)

WT-RBD
55.6 °C
RBD-62
57.9 °C

First derivative (ratio 330/350 norm.)

Temperature [°C]

GPGcP linker (66 aa)

N-ter

C-ter

ACE2

ACE2

Membrane

Profiles Ratio 350 nm / 330 nm for VMN mM of RBD62

Profiles Ratio 350 nm / 330 nm of VM nebulized WT-RBD

SEQUENCE LISTING

```
Sequence total quantity: 48
SEQ ID NO: 1              moltype = DNA   length = 58
FEATURE                   Location/Qualifiers
misc_feature              1..58
                          note = Single strand DNA oligonucleotide
source                    1..58
                          mol_type = other DNA
                          organism = synthetic construct
SEQUENCE: 1
ggcggtagcg gaggcggagg gtcggctagc cattgccctt ttggtgaagt ttttaacg      58

SEQ ID NO: 2              moltype = DNA   length = 76
FEATURE                   Location/Qualifiers
misc_feature              1..76
                          note = Single strand DNA oligonucleotide
source                    1..76
                          mol_type = other DNA
                          organism = synthetic construct
SEQUENCE: 2
ctattacaag tcctcttcag aaataagctt ttgttcggat ccttcaaaag aaagtactac      60
tactctgtat ggttgg                                                     76

SEQ ID NO: 3              moltype = DNA   length = 55
FEATURE                   Location/Qualifiers
misc_feature              1..55
                          note = Single strand DNA oligonucleotide
source                    1..55
                          mol_type = other DNA
                          organism = synthetic construct
SEQUENCE: 3
ggcggtagcg gaggcggagg gtcggctagc catccaaaca tcaccaacct gtgtc           55

SEQ ID NO: 4              moltype = DNA   length = 63
FEATURE                   Location/Qualifiers
misc_feature              1..63
                          note = Single strand DNA oligonucleotide
source                    1..63
                          mol_type = other DNA
                          organism = synthetic construct
SEQUENCE: 4
ctattacaag tcctcttcag aaataagctt ttgttcggat ccctttggtc cacacactgt      60
ggc                                                                   63

SEQ ID NO: 5              moltype = DNA   length = 53
FEATURE                   Location/Qualifiers
misc_feature              1..53
                          note = Single strand DNA oligonucleotide
source                    1..53
                          mol_type = other DNA
                          organism = synthetic construct
SEQUENCE: 5
ggcggtagcg gaggcggagg gtcggctagc catagggtcc aaccaacaga gag             53

SEQ ID NO: 6              moltype = DNA   length = 67
FEATURE                   Location/Qualifiers
misc_feature              1..67
                          note = Single strand DNA oligonucleotide
source                    1..67
                          mol_type = other DNA
                          organism = synthetic construct
SEQUENCE: 6
ctattacaag tcctcttcag aaataagctt ttgttcggat ccgaagttca cacacttgtt      60
cttcacc                                                               67

SEQ ID NO: 7              moltype = DNA   length = 57
FEATURE                   Location/Qualifiers
misc_feature              1..57
                          note = Single strand DNA oligonucleotide
source                    1..57
                          mol_type = other DNA
                          organism = synthetic construct
SEQUENCE: 7
ctgctttggc tgctccagct aatggtcata tgtgcccttt tggtgaagtt tttaacg         57

SEQ ID NO: 8              moltype = DNA   length = 61
FEATURE                   Location/Qualifiers
misc_feature              1..61
                          note = Single strand DNA oligonucleotide
```

-continued

```
source                    1..61
                          mol_type = other DNA
                          organism = synthetic construct
SEQUENCE: 8
gcccgaacca cctccaccag aggatccttc aaaagaaagt actactactc tgtatggttg  60
g                                                                  61

SEQ ID NO: 9              moltype = DNA   length = 45
FEATURE                   Location/Qualifiers
misc_feature              1..45
                          note = Single strand DNA oligonucleotide
source                    1..45
                          mol_type = other DNA
                          organism = synthetic construct
SEQUENCE: 9
tgcccttttg gtgaagtttt taacgccacc aggtttgcct ctgtc                  45

SEQ ID NO: 10             moltype = DNA   length = 54
FEATURE                   Location/Qualifiers
misc_feature              1..54
                          note = Single strand DNA oligonucleotide
source                    1..54
                          mol_type = other DNA
                          organism = synthetic construct
SEQUENCE: 10
ttcaaaagaa agtactacta ctctgtatgg ttggtagccc actccattgg ttgg        54

SEQ ID NO: 11             moltype = DNA   length = 24
FEATURE                   Location/Qualifiers
misc_feature              1..24
                          note = Single strand DNA oligonucleotide
source                    1..24
                          mol_type = other DNA
                          organism = synthetic construct
SEQUENCE: 11
ctacaaactg cctgatgact tcac                                         24

SEQ ID NO: 12             moltype = DNA   length = 22
FEATURE                   Location/Qualifiers
misc_feature              1..22
                          note = Single strand DNA oligonucleotide
source                    1..22
                          mol_type = other DNA
                          organism = synthetic construct
SEQUENCE: 12
gtccaggttg ttgctgttcc ag                                           22

SEQ ID NO: 13             moltype = DNA   length = 75
FEATURE                   Location/Qualifiers
misc_feature              1..75
                          note = Single strand DNA oligonucleotide
source                    1..75
                          mol_type = other DNA
                          organism = synthetic construct
SEQUENCE: 13
ccatgttcgt gtttctggtg ctgctgcctc tggtgtccag caccaacctg tgcccttttg  60
gtgaagtttt taacg                                                   75

SEQ ID NO: 14             moltype = DNA   length = 87
FEATURE                   Location/Qualifiers
misc_feature              1..87
                          note = Single strand DNA oligonucleotide
source                    1..87
                          mol_type = other DNA
                          organism = synthetic construct
SEQUENCE: 14
ccatgttcgt gtttctggtg ctgctgcctc tggtgtccag caccccaaac atcaccaacc  60
tgtgcccttt tggtgaagtt tttaacg                                      87

SEQ ID NO: 15             moltype = DNA   length = 79
FEATURE                   Location/Qualifiers
misc_feature              1..79
                          note = Single strand DNA oligonucleotide
source                    1..79
                          mol_type = other DNA
                          organism = synthetic construct
SEQUENCE: 15
cgacttaaga tcgatgcggc cgcgagctcg aatttttatca atggtgatgg tgatggtgct  60
ttggtccaca cactgtggc                                               79
```

```
SEQ ID NO: 16              moltype = DNA   length = 58
FEATURE                    Location/Qualifiers
misc_feature               1..58
                           note = Single strand DNA oligonucleotide
source                     1..58
                           mol_type = other DNA
                           organism = synthetic construct
SEQUENCE: 16
cgccaccagg tttgcctctg tctatgcctg ggaaaggaag aggtttagca actgtgtg      58

SEQ ID NO: 17              moltype = DNA   length = 55
FEATURE                    Location/Qualifiers
misc_feature               1..55
                           note = Single strand DNA oligonucleotide
source                     1..55
                           mol_type = other DNA
                           organism = synthetic construct
SEQUENCE: 17
caggaagagg tttagcaact gtgtggctga ctggtctgtg ctctacaact ctgcc         55

SEQ ID NO: 18              moltype = DNA   length = 60
FEATURE                    Location/Qualifiers
misc_feature               1..60
                           note = Single strand DNA oligonucleotide
source                     1..60
                           mol_type = other DNA
                           organism = synthetic construct
SEQUENCE: 18
gaagaggttt agcaactgtg tggctgacta ctcttggctc tacaactctg cctccttcag   60

SEQ ID NO: 19              moltype = DNA   length = 65
FEATURE                    Location/Qualifiers
misc_feature               1..65
                           note = Single strand DNA oligonucleotide
source                     1..65
                           mol_type = other DNA
                           organism = synthetic construct
SEQUENCE: 19
cttcagcacc ttcaagtgtt atggagtgag cccacgtaaa ctgaatgacc tgtgtttcac   60
caatg                                                              65

SEQ ID NO: 20              moltype = DNA   length = 57
FEATURE                    Location/Qualifiers
misc_feature               1..57
                           note = Single strand DNA oligonucleotide
source                     1..57
                           mol_type = other DNA
                           organism = synthetic construct
SEQUENCE: 20
ctgactcctt tgtgattagg ggagatgagg tggatcagat tgcccctgga caaacag       57

SEQ ID NO: 21              moltype = DNA   length = 58
FEATURE                    Location/Qualifiers
misc_feature               1..58
                           note = Single strand DNA oligonucleotide
source                     1..58
                           mol_type = other DNA
                           organism = synthetic construct
SEQUENCE: 21
gggagatgag gtgagacaga ttgcccctgg agccacaggc aagattgctg actacaac     58

SEQ ID NO: 22              moltype = DNA   length = 60
FEATURE                    Location/Qualifiers
misc_feature               1..60
                           note = Single strand DNA oligonucleotide
source                     1..60
                           mol_type = other DNA
                           organism = synthetic construct
SEQUENCE: 22
ggtgagacag attgcccctg gacaaacagg cgttattgct gactacaact acaaactgcc   60

SEQ ID NO: 23              moltype = DNA   length = 58
FEATURE                    Location/Qualifiers
misc_feature               1..58
                           note = Single strand DNA oligonucleotide
source                     1..58
                           mol_type = other DNA
                           organism = synthetic construct
```

```
SEQUENCE: 23
gacagcaagg tgggaggcaa ctacaactac ctctttagac tgttcaggaa gagcaagc       58

SEQ ID NO: 24           moltype = DNA  length = 57
FEATURE                 Location/Qualifiers
misc_feature            1..57
                        note = Single strand DNA oligonucleotide
source                  1..57
                        mol_type = other DNA
                        organism = synthetic construct
SEQUENCE: 24
ggtgggaggc aactacaact acctctacag acgtttcagg aagagcaagc tgaaacc        57

SEQ ID NO: 25           moltype = DNA  length = 56
FEATURE                 Location/Qualifiers
misc_feature            1..56
                        note = Single strand DNA oligonucleotide
source                  1..56
                        mol_type = other DNA
                        organism = synthetic construct
SEQUENCE: 25
gagtgaaggg cttcaactgt tacttcccac tcatgtccta tggcttccga ccaacc         56

SEQ ID NO: 26           moltype = DNA  length = 58
FEATURE                 Location/Qualifiers
misc_feature            1..58
                        note = Single strand DNA oligonucleotide
source                  1..58
                        mol_type = other DNA
                        organism = synthetic construct
SEQUENCE: 26
ccaggctggc agcacaccat gtaatggagt gcgcggcttc aactgttact tcccactc       58

SEQ ID NO: 27           moltype = DNA  length = 56
FEATURE                 Location/Qualifiers
misc_feature            1..56
                        note = Single strand DNA oligonucleotide
source                  1..56
                        mol_type = other DNA
                        organism = synthetic construct
SEQUENCE: 27
ctgttacttc ccactccaat cctatggctt ccatccaacc tatggagtgg gctacc         56

SEQ ID NO: 28           moltype = DNA  length = 58
FEATURE                 Location/Qualifiers
misc_feature            1..58
                        note = Single strand DNA oligonucleotide
source                  1..58
                        mol_type = other DNA
                        organism = synthetic construct
SEQUENCE: 28
cttcccactc caatcctatg gcttccgacc aacctttgga gtgggctacc aaccatac       58

SEQ ID NO: 29           moltype = DNA  length = 57
FEATURE                 Location/Qualifiers
misc_feature            1..57
                        note = Single strand DNA oligonucleotide
source                  1..57
                        mol_type = other DNA
                        organism = synthetic construct
SEQUENCE: 29
cctatggctt ccgaccaacc tatggagtgg gctggcaacc atacagggtg gtggtgc        57

SEQ ID NO: 30           moltype = DNA  length = 58
FEATURE                 Location/Qualifiers
misc_feature            1..58
                        note = Single strand DNA oligonucleotide
source                  1..58
                        mol_type = other DNA
                        organism = synthetic construct
SEQUENCE: 30
ccaaccatac agggtggtgg tgctgtcctt tgaaatgctc catgccctg ccacagtg        58

SEQ ID NO: 31           moltype = DNA  length = 58
FEATURE                 Location/Qualifiers
misc_feature            1..58
                        note = Single strand DNA oligonucleotide
source                  1..58
                        mol_type = other DNA
```

-continued

```
                        organism = synthetic construct
SEQUENCE: 31
gtgaagggct tcaactgtta ctttccactc caaccttatg gcttccgacc aacctatg      58

SEQ ID NO: 32           moltype = DNA   length = 66
FEATURE                 Location/Qualifiers
misc_feature            1..66
                        note = Single strand DNA oligonucleotide
source                  1..66
                        mol_type = other DNA
                        organism = synthetic construct
SEQUENCE: 32
gcaagaaggg aggcaactac aactacctct acagacgttt caggaagagc aaactgaaac     60
catttg                                                                66

SEQ ID NO: 33           moltype = AA   length = 139
FEATURE                 Location/Qualifiers
REGION                  1..139
                        note = Protein sequence of modified eUnaG2
source                  1..139
                        mol_type = protein
                        organism = synthetic construct
SEQUENCE: 33
MLEKFVGTWK IESSENFGEY LKAIGAPKEL ADAGDATTPV LYISQKDGDK MTVKIENGPP     60
TFLDTQVSFK LGEEFDEFPS DRRKGVKSVV NLSGEKLVYV QKWDGKETTY VREIKDGKLV    120
VTLTMGDVVA VRSYRRASE                                                 139

SEQ ID NO: 34           moltype = DNA   length = 420
FEATURE                 Location/Qualifiers
misc_feature            1..420
                        note = Nucleic acid sequence of modified eUnaG2
source                  1..420
                        mol_type = other DNA
                        organism = synthetic construct
SEQUENCE: 34
atgttagaaa aatttgttgg cacctggaag atcgaatcct ctgaaaattt tggtgaatac     60
ttgaaggcta tcggtgcccc aaaagaattg gctgatgctg gtgatgctac tactccagtc    120
ttgtacattt ctcaaaagga tggtgataag atgaccgtca agattgaaaa cggtccacca    180
actttttttgg atacccaagt ttctttcaag ttgggtgaag aattcgacga atttccatcc    240
gatagaagaa agggtgttaa gtccgttgtt aacttgtctg gtgagaagtt ggtttacgtt    300
caaaagtggg atggtaaaga aaccacttac gtcagagaaa tcaaggacgg taaattggtt    360
gttactttga ccatgggtga tgttgttgct gttagatctt atagaagggc tctctgaataa    420

SEQ ID NO: 35           moltype = AA   length = 125
FEATURE                 Location/Qualifiers
REGION                  1..125
                        note = DnbALFA amino acid sequence
source                  1..125
                        mol_type = protein
                        organism = synthetic construct
SEQUENCE: 35
MSGEVQLQES GGGLVQPNGS LRLSCNASGV TISALNAMAM GWYRQAPGER RVMVAAVSER     60
GNAMYRESVK GRFTISRDNA NNMVSLQMDN LKPEDTAVYY CHVLEDRGDT FHDYWGQGTQ    120
VTVSS                                                                125

SEQ ID NO: 36           moltype = DNA   length = 375
FEATURE                 Location/Qualifiers
misc_feature            1..375
                        note = DnbALFA nucleic acid sequence
source                  1..375
                        mol_type = other DNA
                        organism = synthetic construct
SEQUENCE: 36
atgagcggtg aagttcagct gcaagaaagc ggtggtggtc tggttcagcc taatggtagc     60
ctgcgtctga gctgtaacgc aagcggtgtt accattagcg cactgaatgc aatggcaatg    120
ggttggtatc gtcaggcacc gggtgaacgt cgtgttatgg ttgcagcagt tagcgaacgt    180
ggtaatgcaa tgtatcgtga aagcgttaaa ggtcgttta ccatttctcg tgataatgct     240
aacaatatgg ttagcctgca gatggataat ctgaaaccgg aagataccgc agtgtattat    300
tgtcatgttc tggaagatcg tggtgatact tttcatgatt attggggtca gggcacccag    360
gttaccgtta gcagc                                                     375

SEQ ID NO: 37           moltype = AA   length = 1273
FEATURE                 Location/Qualifiers
source                  1..1273
                        mol_type = protein
                        note = Severe acute respiratory syndrome coronavirus 2
                        organism = Severe acute respiratory syndrome-related
                         coronavirus
SEQUENCE: 37
```

```
MFVFLVLLPL VSSQCVNLTT RTQLPPAYTN SFTRGVYYPD KVFRSSVLHS TQDLFLPFFS    60
NVTWFHAIHV SGTNGTKRFD NPVLPFNDGV YFASTEKSNI IRGWIFGTTL DSKTQSLLIV   120
NNATNVVIKV CEFQFCNDPF LGVYYHKNNK SWMESEFRVY SSANNCTFEY VSQPFLMDLE   180
GKQGNFKNLR EFVFKNIDGY FKIYSKHTPI NLVRDLPQGF SALEPLVDLP IGINITRFQT   240
LLALHRSYLT PGDSSSGWTA GAAAYYVGYL QPRTFLLKYN ENGTITDAVD CALDPLSETK   300
CTLKSFTVEK GIYQTSNFRV QPTESIVRFP NITNLCPFGE VFNATRFASV YAWNRKRISN   360
CVADYSVLYN SASFSTFKCY GVSPTKLNDL CFTNVYADSF VIRGDEVRQI APGQTGKIAD   420
YNYKLPDDFT GCVIAWNSNN LDSKVGGNYN YLYRLFRKSN LKPFERDIST EIYQAGSTPC   480
NGVEGFNCYF PLQSYGFQPT NGVGYQPYRV VVLSFELLHA PATVCGPKKS TNLVKNKCVN   540
FNFNGLTGTG VLTESNKKFL PFQQFGRDIA DTTDAVRDPQ TLEILDITPC SFGGVSVITP   600
GTNTSNQVAV LYQDVNCTEV PVAIHADQLT PTWRVYSTGS NVFQTRAGCL IGAEHVNNSY   660
ECDIPIGAGI CASYQTQTNS PRRARSVASQ SIIAYTMSLG AENSVAYSNN SIAIPTNFTI   720
SVTTEILPVS MTKTSVDCTM YICGDSTECS NLLLQYGSFC TQLNRALTGI AVEQDKNTQE   780
VFAQVKQIYK TPPIKDFGGF NFSQILPDPS KPSKRSFIED LLFNKVTLAD AGFIKQYGDC   840
LGDIAARDLI CAQKFNGLTV LPPLLTDEMI AQYTSALLAG TITSGWTFGA GAALQIPFAM   900
QMAYRFNGIG VTQNVLYENQ KLIANQFNSA IGKIQDSLSS TASALGKLQD VVNQNAQALN   960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                    1273
```

```
SEQ ID NO: 38              moltype = AA   length = 196
FEATURE                    Location/Qualifiers
REGION                     1..196
                           note = B52 amino acid sequence
source                     1..196
                           mol_type = protein
                           organism = synthetic construct
SEQUENCE: 38
TNLCPFGEVF NATRFASVYA WNRKRFSNCV ADYSVLYNSA SFSTFKCYGV SPTKLNDLCF    60
TNVYADSFVI RGDEVRQIAP GQTGKIADYN YKLPDDFTGC VIAWNSNNLD SKVGGNYNYL   120
YRLFRKSKLK PFERDISTEI YQAGSTPCNG VKGFNCYFPL QPYGFRPTYG VGYQPYRVVV   180
LSFELLHGPA TVCGPK                                                   196
```

```
SEQ ID NO: 39              moltype = AA   length = 196
FEATURE                    Location/Qualifiers
REGION                     1..196
                           note = B62 amino acid sequence
source                     1..196
                           mol_type = protein
                           organism = synthetic construct
SEQUENCE: 39
TNLCPFGEVF NATRFASVYA WNRKRFSNCV ADYSVLYNSA SFSTFKCYGV SPTKLNDLCF    60
TNVYADSFVI RGDEVRQIAP GQTGKIADYN YKLPDDFTGC VIAWNSNNLD SKKGGNYNYL   120
YRLFRKSKLK PFERDTSMEI YQAGNTPCNG VKGFNCYFPL QSYGFRPTYG VGYQPYRVVV   180
LSFELLHAPA TVCGPK                                                   196
```

```
SEQ ID NO: 40              moltype = AA   length = 196
FEATURE                    Location/Qualifiers
REGION                     1..196
                           note = B71 amino acid sequence
source                     1..196
                           mol_type = protein
                           organism = synthetic construct
SEQUENCE: 40
TNLCPFGEVF NATRFASVYA WNRKRFSNCV ADYSWLYNSA SFSTFKCYGV SPTKLNDLCF    60
TNVYADSFVI RGDEVDQIAP GQTGVIADYN YKLPDDFTGC VIAWNSNNLD SKKGGNYNYL   120
YRLFRKSKLK PFERDTSMEI YQAGNTPCNG VKGFNCYFPL QSYGFRPTYG VGYQPYRVVV   180
LSFELLHAPA TVCGPK                                                   196
```

```
SEQ ID NO: 41              moltype = AA   length = 66
FEATURE                    Location/Qualifiers
REGION                     1..66
                           note = linker sequence GPGcP amino acid sequence
source                     1..66
                           mol_type = protein
                           organism = synthetic construct
SEQUENCE: 41
AGSGGSGGSG GSPVPSTPPT PSPSTPPTPS PSGGSGNSSG SGGSPVPSTP PTPSPSTPPT    60
PSPSAS                                                               66
```

```
SEQ ID NO: 42              moltype = AA   length = 55
FEATURE                    Location/Qualifiers
REGION                     1..55
                           note = linker NGL amino acid sequence
source                     1..55
                           mol_type = protein
```

-continued

```
                        organism = synthetic construct
SEQUENCE: 42
SGGGGSGGGG NGSNGSGGSN GSNGSGGSNG SNGSGGSNGS NGSGGSGGGG SGGGG          55

SEQ ID NO: 43             moltype = AA  length = 455
FEATURE                   Location/Qualifiers
REGION                    1..455
                          note = Dimer amino acid sequence
source                    1..455
                          mol_type = protein
                          organism = synthetic construct
SEQUENCE: 43
TNLCPFGEVF NATRFASVYA WNRKRFSNCV ADYSVLYNSA SFSTFKCYGV SPTKLNDLCF    60
TNVYADSFVI RGDEVRQIAP GQTGKIADYN YKLPDDFTGC VIAWNSNNLD SKKGGNYNYL   120
YRLFRKSKLK PFERDTSMEI YQAGNTPCNG VKGFNCYFPL QSYGFRPTYG VGYQPYRVVV   180
LSFELLHAPA TVCGPKAGSG GSGGSGGSPV PSTPPTPSPS TPPTPSPSGG SGNSSGSGGS   240
PVPSTPPTPS PSTPPTPSPS ASCPFGEVFN ATRFASVYAW NRKRFSNCVA DYSWLYNSAS   300
FSTFKCYGVS PTKLNDLCFT NVYADSFVIR GDEVDQIAPG QTGVIADYNY KLPDDFTGCV   360
IAWNSNNLDS KKGGNYNYLY RLFRKSKLKP FERDTSMEIY QAGNTPCNGV KGFNCYFPLQ   420
SYGFRPTYGV GYQPYRVVVL SFELLHAPAT VCGPK                              455

SEQ ID NO: 44             moltype = AA  length = 60
FEATURE                   Location/Qualifiers
REGION                    1..60
                          note = Ace2 amino acid sequence
source                    1..60
                          mol_type = protein
                          organism = synthetic construct
SEQUENCE: 44
MSSSSWLLLS LVAVTAAQST IEEQAKTFLD KFNHEAEDLF YQSSLASWNY NTNITEENVQ   60

SEQ ID NO: 45             moltype = AA  length = 40
FEATURE                   Location/Qualifiers
REGION                    1..40
                          note = Arg319-Phe541 of SEQ ID NO: 37
source                    1..40
                          mol_type = protein
                          organism = synthetic construct
SEQUENCE: 45
GIYQTSNFRV QPTESIVRFP NITNLCPFGE VFNATRFASV                          40

SEQ ID NO: 46             moltype = DNA  length = 588
FEATURE                   Location/Qualifiers
misc_feature              1..588
                          note = B52 nucleotide sequence
source                    1..588
                          mol_type = other DNA
                          organism = synthetic construct
SEQUENCE: 46
accaacctgt gcccttttgg tgaagttttt aacgccacca ggtttgcctc tgtctatgcc   60
tggaacagga agaggtttag caactgtgtg gctgactact ctgtgctcta caactctgcc  120
tccttcagca ccttcaagtg ttatggagtg agcccaacca aactgaatga cctgtgtttc  180
accaatgtct atgctgactc ctttgtgatt aggggagatg aggtgagaca gattgcccct  240
ggacaaacag gcaagattgc tgactacaac tacaaactgc ctgatgactt cacaggctgt  300
gtgattgcct ggaacagcaa caacctggac agcaaggtgg gaggcaacta caactacctc  360
tacagactgt tcaggaagag caaactgaaa ccatttgaga gggacatcag cacagagatt  420
taccaggctg gcagcacacc atgtaatgga gtgaagggct tcaactgtta ctttccactc  480
caaccctatg gcttccgacc aacctatgga gtgggctacc aaccatacag ggtggtggtg  540
ctgtcctttg aactgctcca tggccctgcc acagtgtgtg gaccaaag             588

SEQ ID NO: 47             moltype = DNA  length = 588
FEATURE                   Location/Qualifiers
misc_feature              1..588
                          note = B62 nucleotide sequence
source                    1..588
                          mol_type = other DNA
                          organism = synthetic construct
SEQUENCE: 47
accaacctgt gcccttttgg tgaagttttt aacgccacca ggtttgcctc tgtctatgcc   60
tggaacagga agaggtttag caactgtgtg gctgactact ctgtgctcta caactctgcc  120
tccttcagca ccttcaagtg ttatggagtg agcccaacca aactgaatga cctgtgtttc  180
accaatgtct atgctgactc ctttgtgatt aggggagatg aggtgagaca gattgcccct  240
ggacaaacag gcaagattgc tgactacaac tacaaactgc ctgatgactt cacaggctgt  300
gtgattgcct ggaacagcaa caacctggac agcaaggtgg gaggcaacta caactacctc  360
tacagactgt tcaggaagag caaactgaaa ccatttgaga gggacaccag catggagatt  420
taccaggctg gcaacacgcc atgtaatgga gtgaagggct tcaactgtta ctttccactc  480
caatcctatg gcttccgacc aacctatgga gtgggctacc aaccatacag ggtggtggtg  540
ctgtcctttg aactgctcca tgccctgcc acagtgtgtg gaccaaag              588
```

-continued

```
SEQ ID NO: 48         moltype = DNA   length = 579
FEATURE               Location/Qualifiers
misc_feature          1..579
                      note = B71 nucleotide sequence
source                1..579
                      mol_type = other DNA
                      organism = synthetic construct
SEQUENCE: 48
tgccctttg gtgaagtttt taacgccacc aggtttgcct ctgtctatgc ctggaacagg   60
aagaggttta gcaactgtgt ggctgactac tcttggctct acaactctgc ctccttcagc  120
accttcaagt gttatggagt gagcccaacc aaactgaatg acctgtgttt caccaatgtc  180
tatgctgact cctttgtgat taggggagat gaggtggatc agattgcccc tggacaaaca  240
ggcgttattg ctgactacaa ctacaaactg cctgatgact tcacaggctg tgtgattgcc  300
tggaacagca acaacctgga cagcaagaag ggaggcaact acaactacct ctacagactg  360
ttcaggaaga gcaaactgaa accatttgag agggacacca gcatggagat ttaccaggct  420
ggcaacacgc catgtaatgg agtgaagggc ttcaactgtt actttccact ccaatcctat  480
ggcttccgac caacctatgg agtgggctac caaccataca gggtggtggt gctgtccttt  540
gaactgctcc atgcccctgc cacagtgtgt ggaccaaag                         579
```

METHODS AND COMPOSITIONS FOR TREATING CORONAVIRAL INFECTIONS

RELATED APPLICATIONS

This application is a Continuation of PCT Patent Application No. PCT/IL2021/051154 having International filing date of Sep. 22, 2021, which claims the benefit of priority of Israeli Patent Application No. 277546 filed on Sep. 23, 2020 and under 35 USC § 119 (e) U.S. Provisional Patent Application No. 63/125,984 filed on Dec. 16, 2020. The contents of the above applications are all incorporated by reference as if fully set forth herein in their entirety.

SEQUENCE LISTING STATEMENT

The XML file, entitled 95459SequenceListing.xml, created on Mar. 16, 2023, comprising 68,112 bytes, submitted concurrently with the filing of this application is incorporated herein by reference.

FIELD AND BACKGROUND OF THE INVENTION

The present invention, in some embodiments thereof, relates to peptides and RNA encoding the peptides for treatment or prevention of Coronavirus infections.

Since December 2019 when several cases of COVID-19 were reported in Wuhan, China, twenty million cases were reported worldwide, with over 700,000 deaths up to the date. COVID-19 is closely related to the SARS-COV virus. Disease progression of COVID-19 goes through a number of stages. The initial stage, which lasts from 2-14 days (usually 5-6 days) from infection is asymptomatic. A certain proportion of patients never produce any symptoms. Of those who develop symptoms, they are mostly mild (80% of those who develop symptoms). From the remaining 20%, about half will develop severe symptoms, which require hospitalization in intensive care units. The mortality rate, from those developing symptoms is 2-5%. The numbers given above are average, and change dramatically with age. At young age most of the infected people will be asymptomatic, while over the age of 70 about 80% will have symptoms. Moreover, as the age progresses, symptom severity increases. The major complication of severe infection is pneumonia, which can develop into acute respiratory distress syndrome (ARDS). In addition, COVID-19 has been linked to cardiovascular sequelae, such as myocardial injury, arrhythmias, cardiomyopathy and heart failure, acute kidney injury, neurological complications, and acute ischemic stroke. Developing severe symptoms and death is strongly related to background conditions. The strongest relation is to age, with the risk to people under 50 being very small, while the risk peaks for people over the age of 75. In addition, chronic kidney disease, chronic obstructive pulmonary disease, immunocompromised state, obesity, heart conditions and type 2 diabetes are linked to higher incidents of sever disease.

CoV-2 is presumed to infect people mostly though inhalation of viral particles, which can be airborne, in droplets or otherwise through infection through touching infected surfaces. The Spike protein on the CoV-2 surface binds to the human ACE2 protein, which serves as its receptor. The homotrimeric spike glycoprotein is made up from S1 and S2 subunits. Its binding and subsequent cleavage by the host protease TMPRSS2 results in the fusion between cell and viral membranes for cell entry. Blocking the ACE2 receptors by specific antibodies voids viral entry [3-5]. Interestingly, the CoV-2 receptor-binding domain (RBD) exhibits significantly higher binding affinity to ACE2 than the SARS-CoV RBD, which was speculated to relate to the higher infectivity of COVID-19 in relation to SARS. After membrane fusion, the virus enters through the endosomal pathway and the viral RNA is released into the host cell. The viral RNA is then translated into a viral polyprotein, which is cleaved into small products by viral proteases (papain-like protease— PLpro). Viral proteins and genome RNA are subsequently assembled into virions in the ER and Golgi and then transported and released out of the cell.

An unprecedented amount of effort has been invested in finding a cure for COVID-19. One strategy is to find a vaccine. A second, complementary strategy is to find drugs that will alleviate the clinical symptoms of COVID-19, and thus transform it from being a global pandemic to another treatable infectious disease.

Background art includes Baig et al., Drugs in R&D (2020) 20:161-169; Starr et al., 2020, Cell 182, 1295-1310 and Huang et al., Acta Pharmacologica Sinica (2020) 41:1141-1149.

SUMMARY OF THE INVENTION

According to an aspect of the present invention there is provided a polypeptide comprising an amino acid sequence of SARS COV-2 receptor-binding domain (RBD), wherein the amino acid sequence comprises a modification at position 358 and at least two additional modifications at positions 484, 498 and 501, wherein the numbering of the positions of the modifications is according to UniProtKB-PODTC2 (SEQ ID NO: 37), wherein the polypeptide binds soluble, monomeric angiotensin-converting enzyme 2 (ACE2) receptor when expressed on the surface of yeast cells with at least 50 fold higher affinity than the wild-type RBD having an amino acid sequence as set forth in SEQ ID NO: 45, when assayed under identical conditions, wherein the polypeptide comprises at least 170 amino acids of the RBD.

According to an aspect of the present invention there is provided an isolated polypeptide comprising an amino acid sequence at least 99% identical to SEQ ID NO: 38, 39 or 40.

According to an aspect of the present invention there is provided an isolated polynucleotide encoding the polypeptide described herein.

According to an aspect of the present invention there is provided a dimer comprising two monomers linked by a linker, wherein each of the two monomers comprises an amino acid sequence encoding SARS-COV-2 receptor-binding domain (RBD), wherein each of the monomers binds soluble, monomeric angiotensin-converting enzyme 2 receptor when expressed on the surface of yeast cells with at least 50 fold higher affinity than the wild-type RBD having an amino acid sequence as set forth in SEQ ID NO: 45, when assayed under identical conditions.

According to an aspect of the present invention there is provided an isolated polynucleotide, encoding the dimer described herein.

According to an aspect of the present invention there is provided a vaccine comprising the isolated polypeptide described herein, the isolated polynucleotide described herein, or the dimer described herein, and an immunologically acceptable carrier.

According to an aspect of the present invention there is provided a pharmaceutical composition comprising as an active ingredient the isolated polypeptide described herein, the isolated polynucleotide described herein or the dimer described herein, and a pharmaceutically acceptable carrier.

According to an aspect of the present invention there is provided a nucleic acid construct comprising the isolated polynucleotide described herein and a cis-regulatory element driving expression of the polynucleotide.

According to an aspect of the present invention there is provided a method of treating a coronavirus infection in a subject in need thereof, comprising administering to the subject a therapeutically effective amount of the polypeptide described herein, the isolated polynucleotide described herein or the dimer described herein, thereby treating the coronavirus infection.

According to an aspect of the present invention there is provided an article of manufacture comprising the polypeptide described herein and an anti-inflammatory agent.

According to an aspect of the present invention there is provided a fusion protein comprising a yeast anchoring protein fused to a ligand-inducible fluorescent polypeptide.

According to an aspect of the present invention there is provided a cell expressing the fusion protein described herein.

According to an aspect of the present invention there is provided an isolated polypeptide comprising an amino acid sequence at least 99% identical to the sequence as set forth in SEQ ID NO: 33.

According to an aspect of the present invention there is provided an isolated polynucleotide encoding the fusion protein described herein or the isolated polypeptide described herein.

According to an aspect of the present invention there is provided a method of analyzing the expression of a protein of interest on the surface of a yeast cell comprising:

(a) transfecting the yeast cell with a polynucleotide encoding the fusion protein described herein under conditions that allows display of the fusion protein on the surface of the yeast cell;

(b) contacting the yeast cell with the ligand so as to induce fluorescence of the fluorescent polypeptide; and (c) analyzing the amount of fluorescence emitted by the fluorescent polypeptide, wherein the amount of fluorescence is indicative of the expression level of the protein of interest.

According to some embodiments of the invention, the polypeptide comprises modifications at each of the positions 358, 484, 498 and 501.

According to some embodiments of the invention, the polypeptide further comprises a modification at position 460.

According to some embodiments of the invention, the modification is a substitution.

According to some embodiments of the invention, the modification at position 358 comprises a I358F substitution, wherein the modification at position 484 comprises a E498K substitution, wherein the modification at position 498 comprises a Q498R substitution, or the modification at position 501 comprises a N501Y substitution.

According to some embodiments of the invention, the modification at position 460 comprises a N460K substitution.

According to some embodiments of the invention, the polypeptide comprises the substitutions:

(i) I358F, N460K, E484K, S494P, Q498R and N501Y;

(ii) I358F, N460K, E484K, Q498R and N501Y;

(iii) I358F, E484K, Q498R and N501Y;

(iv) I358F, V445K, N460K, I468T, T470M, S477N, E484K, Q498R and N501Y; or (v) I358F, V367W, R408D, K417V, V445K, N460K, I468T, T470M, S477N, E484K, Q498R and N501Y.

According to some embodiments of the invention, the polypeptide comprises an amino acid sequence at least 99% identical to SEQ ID NOs: 38 (B52), 39 (B62) or 40 (B71).

According to some embodiments of the invention, the polypeptide comprises no more than 250 amino acids of the S1 subunit of the spike protein of SARS COV-2.

According to some embodiments of the invention, the isolated polypeptide is no longer than 250 amino acids in length.

According to some embodiments of the invention, the polypeptide is for use in treating a coronavirus infection.

According to some embodiments of the invention, the isolated polynucleotide is an mRNA.

According to some embodiments of the invention, the isolated polynucleotide has a nucleic acid sequence as set forth in SEQ ID NOs: 46, 47 or 48.

According to some embodiments of the invention, each of the monomers comprises a modification at position 358, wherein the numbering of the position of the modification is according to UniProtKB-PODTC2 (SEQ ID NO: 37).

According to some embodiments of the invention, the amino acid sequence of the two monomers is at least 99% identical to SEQ ID NO: 38, 39 or 40.

According to some embodiments of the invention, a first of the two monomers comprises an amino acid sequence as set forth in SEQ ID NO: 39 and a second of the two monomers comprises an amino acid sequence as set forth in SEQ ID NO: 40.

According to some embodiments of the invention, the linker is a peptide linker.

According to some embodiments of the invention, the peptide linker comprises an amino acid sequence as set forth in SEQ ID NO: 41 or 42.

According to some embodiments of the invention, the dimer has an amino acid sequence at least 99% identical to SEQ ID NO: 43.

According to some embodiments of the invention, the dimer is for use in treating a coronavirus infection.

According to some embodiments of the invention, the vaccine further comprises an adjuvant.

According to some embodiments of the invention, the pharmaceutical composition is formulated for inhalation.

According to some embodiments of the invention, the coronavirus infection is COVID-19.

According to some embodiments of the invention, the coronavirus is SAR-COV-2, Middle East respiratory syndrome Coronavirus (MERS-COV) or severe acute respiratory syndrome Coronavirus (SARS-COV).

According to some embodiments of the invention, the administering is effected by inhalation.

According to some embodiments of the invention, the anti-inflammatory agent comprises interferon I.

According to some embodiments of the invention, the yeast anchoring protein comprises yeast mating factor agglutinin A protein.

According to some embodiments of the invention, the fusion protein further comprises a protein of interest.

According to some embodiments of the invention, the cell is a yeast cell.

According to some embodiments of the invention, the ligand inducible fluorescent polypeptide is eUnaG2.

According to some embodiments of the invention, an amino acid sequence of the eUnaG2 is set forth in SEQ ID NO: 33.

According to some embodiments of the invention, the fluorescent polypeptide is eUnaG2.

According to some embodiments of the invention, an amino acid sequence of the eUnaG2 is set forth in SEQ ID NO: 33.

According to some embodiments of the invention, the ligand is bilirubin.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 eUnaG2 mutations incorporated for stronger fluorescence and/or higher expression levels, shown on the structure of the wild type protein.

FIGS. 3A-D Comparing wild-type RBD to RBD-52. (A) shows binding affinity as determined using titration of ACE2 on yeast surface bound RBD. (B) shows the results of biolayer interferometry technology as implemented on ForteBio's Octet® RED96 instrument with ACE2 immobilized on the surface. The binding constants were calculated using 3 different concentrations of RBD (of which a representative one is shown). (C) ACE2 activity was determined on ACE2 expressing HEK293 cells using SensoLyte® 390 ACE2 Activity Assay Kit (Fluorimetric), which measures Mc-Ala/Dnp fluorescence resonance energy transfer (FRET) peptide. In the FRET peptide, the fluorescence of Mc-Ala is quenched by Dnp. Upon cleavage into two separate fragments by ACE2, the fluorescence of Mc-Ala is recovered, and can be monitored at excitation/emission=330/390 nm. RBD-52 was added at a concentration of 10 nM (10000-fold the affinity) for 24 hr prior to the ACE2 activity measurement. (D) thermal denaturation of WT-RBD and RBD-62 as determined using a Tycho™ NT.6 Nano-DSF (NanoTemper).

FIGS. 7A-C show the fluorescence ratios of RBD62, WT-RBD and Interferon-α after nebulization by the Acrogen® Solo. FIG. 7A shows results for nebulization of RBD62 at four concentrations from 2.4 to 19 µM. FIG. 7B shows results for nebulization of WT RBD at 3.69 and 7.36 µM. FIG. 7C shows that the IFN-α fully recovers after nebulization at this concentrations range. The profile is as expected and the mid point for unfolding Tm, increase at the higher concentrations according to the increase of dimerization of the protein.

7 ume was 200 μl on ~120,000 cells. The red numbers in the graphs represent the % of non-fluorescent cells: the first run at the top, the last run at the bottom.

Figure 10:
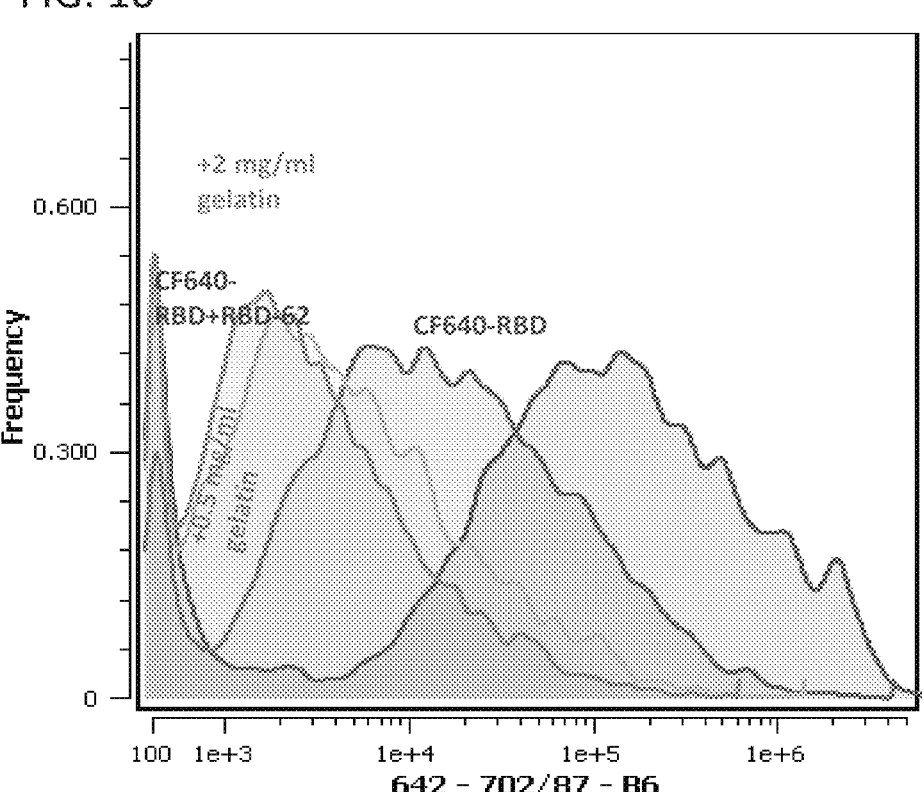

FIG. 10 HEK-ACE2 cells were treated with labeled (CF640) WT RBD and chased with 200 μl of aerosols (using vibrating mash (VM) nebulizer) containing 2 μg RBD-62 alone or with 0.5 or 2 mg/ml of gelatin. Clearly, gelatin is increasing the efficiency of RBD-62 after nebulization.

Figure 11:
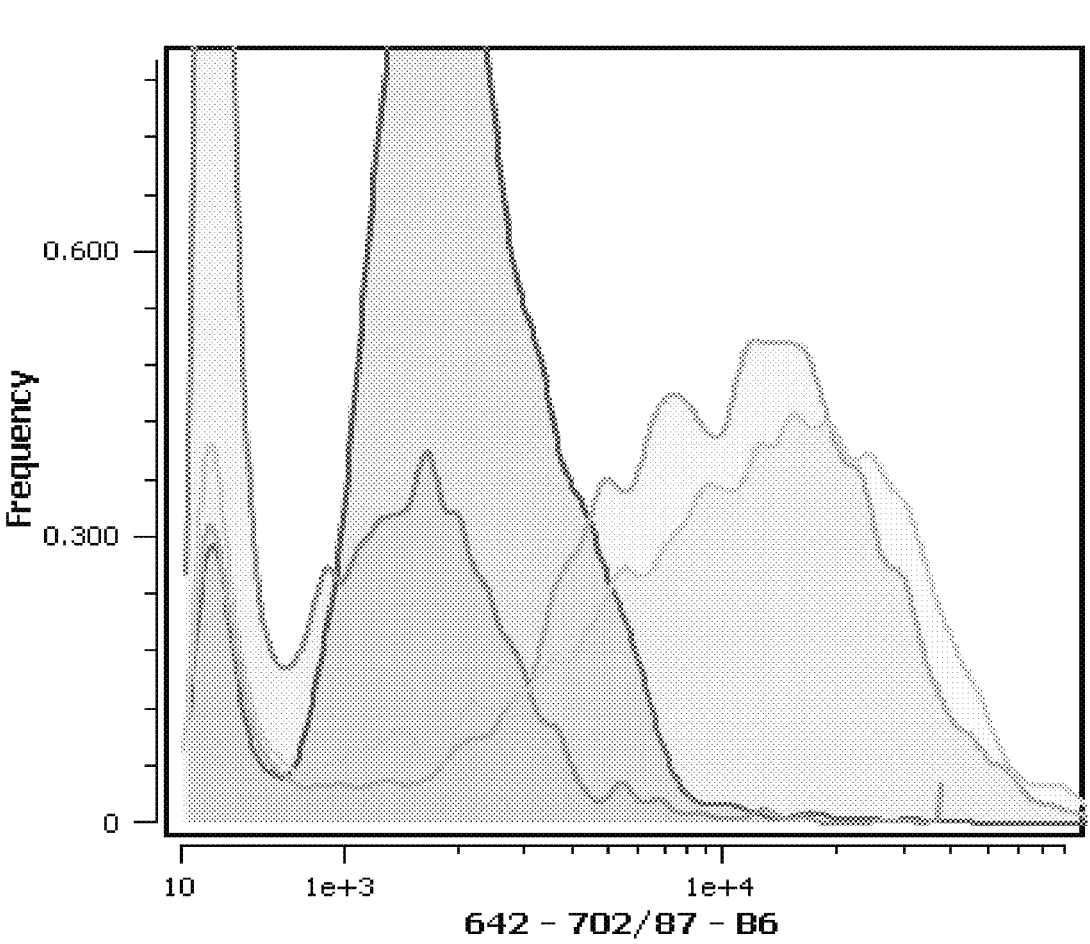

FIG. 11 shows induction of STAT1-phosphorylation upon treating HeLa cells with IFNα2 or IFNβ after nebulization, at concentration of 30 μg/ml+0.5 mg/ml gelatin. IFNα2 on HeLa (light blue line) or double knock out-HeLa (dark blue line) or IFNβ (yellow and orange for WT and double knock-out respectively) were nebulized for cell treatment for 30 min.

DESCRIPTION OF SPECIFIC EMBODIMENTS OF THE INVENTION

The present invention, in some embodiments thereof, relates to peptides and RNA encoding the peptides for treatment of Coronavirus infections.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The mechanism of entry of SARS-COV-2 is through binding the ACE2 protein that is anchored on the membrane of cells of the respiratory system. The present inventors have now engineered ultra-tight binding protein inhibitors of ACE2, with the binding being almost non-reversible. The inhibitors, which are based on the natural receptor-binding domain (RBD) of the spike protein (S-protein) of SARS-COV-2, have >1000-fold tighter binding than the wild-type (WT) RBD (see Table 4). The mutant inhibitors were assessed for inhibition of viral entry, improved protein-stability, and lack of inhibition of enzymatic activity of ACE2 (which plays an important role in inducing an immune response and keeping blood pressure under control).

The novel peptide inhibitors described herein should be resistant against alterations and mutations of the virus, as the engineered inhibitor binds the cell surface receptor, which is not affected by mutations of the virus. As both the original SARS virus that emerged in 2002 and the current SARS-COV-2 virus use the same entry port (ACE2), the peptide inhibitors should have a broad specificity and be useful also for treating diseases of future alterations and strains of the corona virus.

Thus, according to a first aspect of the present invention, there is provided a polypeptide comprising an amino acid sequence of SARS-COV-2 receptor-binding domain (RBD), wherein said amino acid sequence comprises a modification at position 358 and at least two additional modifications at two positions selected from the group consisting of 484, 498 and 501, wherein the numbering of the positions of the modifications is according to UniProtKB-PODTC2 (SEQ ID NO: 37), wherein said polypeptide binds soluble, monomeric angiotensin-converting enzyme 2 (ACE2) receptor when expressed on the surface of yeast cells with at least 50 fold higher affinity than the wild-type RBD having an amino acid sequence as set forth in SEQ ID NO: 45, when assayed under identical conditions, wherein said polypeptide comprises at least 170 amino acids of said RBD.

As used herein "SARS-COV-2 receptor binding domain (RBD)" refers to the receptor (ACE2) binding domain of SARS-COV-2 of SPIKE, residues Arg319-Phe541 of SPIKE (as set forth in SEQ ID NO: 45). The full length amino acid sequence of SPIKE is set forth in SEQ ID NO: 37.

The polypeptides described herein bind to soluble monomeric angiotensin-converting enzyme 2 (ACE2) receptor when expressed on the surface of yeast cells.

As used herein "soluble" refers to the portion of ACE2 which is devoid of a transmembrane domain (as defined by coordinates 741-761 of the human ACE2 protein) and the membrane proximal extracellular portion 616-741, and optionally also the intracellular domain (762 till end 805). Amino acid coordinates correspond to SEQ ID NO: 44.

As used herein "ACE2" refers to Angiotensin-converting enzyme 2 (ACE2) E.C. 3.4.17.23 (GenBank Accession No. NP_068576), which is encoded in human by the ACE2 gene. ACE2 is an enzyme attached to the cell membranes of cells in the lungs, arteries, heart, kidney, and intestines. ACE2 lowers blood pressure by catalysing the hydrolysis of angiotensin II (a vasoconstrictor peptide) into angiotensin (1-7) (a vasodilator). ACE2 counters the activity of the related angiotensin-converting enzyme (ACE) by reducing the amount of angiotensin-II and increasing Ang (1-7). ACE2 also serves as the entry point into cells for Coronaviruses, including HCoV-NL63, SARS-COV, and SARS-COV-2. The human version of the enzyme is often referred to as hACE2.

According to a specific embodiment, the ACE2 is human ACE2.

In order to express the polypeptides of this aspect of the present invention on the surface of yeast cells (e.g. *Pichia pastoris* or *Saccharomyces cerevisiae* cells), preferably they are expressed as fusion proteins together with anchoring protein such as yeast mating agglutinin factor A protein, as known in the art. Other yeast anchoring proteins include, but are not limited to Cwp1, Cwp2, Gaslp, Yap3p, Flo1p, Crh2p, Pir1, Pir2, Pir4, Icwp, HpSEDI, HpGASI, HpTIPI, HPWPI, Hwplp, Als3p, Rbt5p.

Vectors for expressing the polypeptides in yeast cells include Ylp-based vectors, such as Ylp5, YRp vectors, such as YRp17, YBp vectors such as YEp13 and YCp vectors, such as YCp19. Other examples of the YEp vectors include YEp24, YEp51, and YBp52, which are cloning and expression vehicles useful in the introduction of genetic constructs into *S. cerevisiae* (see, e.g., Broach et al. (1983) in Experimental Manipulation of Gene Expression, ed. M. Inouye Academic Press, p. 83). These vectors are also shuttle vectors in that they can replicate in *E. coli* due the presence of the pBR322 ori, and in *S. cerevisiae* due to the replication determinant of the yeast 2 micron plasmid.

Suitable promoters for function in yeast include the promoters for metallothionein, 3-phosphoglycerate kinase (Hitzeman et al., J. Biol. Chem. 255, 2073 (1980) or other glycolytic enzymes (Hess et al., J. Adv. Enzyme Req. 7, 149 (1968); and Holland et al. Biochemistry 17, 4900 (1978)), such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phospho-glucose isomerase, and glucokinase. Suitable vectors and promoters for use in yeast expression are further described in R. Hitzeman et al., EP073, 657. Other suitable promoters for expression in yeast include the promoters from GAL1 (galactose), PGK (phosphoglycerate kinase), ADH (alcohol dehydrogenase), AOX1 (alcohol oxidase), HIS4 (histidinol dehydrogenase), and the like. Still other promoters, which have the additional advantage of transcription controlled by growth conditions, are the promoter regions for alcohol dehydrogenase 2, isocytochrome C, acid phosphatase, degradative enzymes associated with nitrogen metabolism, and the afore-mentioned metallothionein and glyceraldehyde-3-phosphate dehydrogenase, as well as enzymes responsible for maltose and galactose utilization. Finally, promoters that are active in only one of the two haploid mating types may be appropriate in certain circumstances. Among these hapioid-specific promoters, the phero-mone promoters MFa1 and MFα1 are of particular interest.

Once the amount of polypeptide displayed on the yeast surface is determined (e.g. using a fluorescent protein which is co-expressed with the polypeptide, as described in the Examples section herein below, or via a labelled antibody, as known in the art), it is possible to determine the binding affinity for soluble ACE2. Analysis of fluorescence may be carried out as known in the art (for example by Fluorescence Activated Cell Sorting (FACS or flow cytometry).

As mentioned, the polypeptides of this aspect of the present invention, bind soluble, monomeric angiotensin-converting enzyme 2 (ACE2) receptor, when expressed on the surface of yeast cells, with at least 50 fold, 100 fold, 200 fold, 300 fold, 400 fold, 500 fold, 600 fold, 700 fold, 800 fold, 900 fold or even 1000 fold higher affinity than the wild-type RBD having an amino acid sequence as set forth in SEQ ID NO: 37, when assayed under identical conditions.

In particular, the polypeptides of this aspect of the present invention bind to ACE2 with a $K_D$ of less than 200 pM, less than 20 pM and even less than 10 pM, as measured in a yeast display assay.

As used herein the term "$K_D$" refers to the equilibrium dissociation constant between the polypeptide variant of the RBD of Spike and hACE2.

According to a specific embodiment, the $K_D$ is below 0.3 nM (e.g., 0.01-0.1 nM, 0.01-0.09 nM, 0.01-0.08 nM, 0.01-0.07 nM, 0.01-0.06 nM, 0.01-0.05 nM, 0.01-0.04 nM, 0.01-0.03 nM, 0.01-0.02 nM, 0.01 nM), as determined by ForteBio's Octet® RED96 Surface interferometry e.g., where hACE2 is the SOLUBLE analyte.

According to a particular embodiment, the RBD polypeptides of this aspect of the present invention comprises at least 170 consecutive amino acids of the native sequence of the RBD of SARS-COV-2, at least 180 consecutive amino acids of the native sequence of RBD of SARS-COV-2, at least 190 consecutive amino acids of the native sequence of RBD of SARS-COV-2, at least 200 consecutive amino acids of the native sequence of RBD of SARS-COV-2, at least 210 consecutive amino acids of the native sequence of RBD of SARS-COV-2, at least 220 consecutive amino acids of the native sequence of RBD of SARS-COV-2. For example, the RBD polypeptides described herein preferably comprise amino acids 330-516 of the RBD of the S1 subunit of the spike protein of SARS COV-2.

For the purpose of this invention, the term "consecutive amino acids" also includes the mutations which are disclosed herein.

According to additional embodiments, the polypeptides comprise no more than 250 amino acids of the S1 subunit of the spike protein of SARS COV-2.

The polypeptides described herein are typically no longer than 250 amino acids, 260 amino acids, 270 amino acids, 280 amino acids, 290 amino acids or 300 amino acids.

The terms "peptide" and "polypeptide" which are interchangeably used herein encompass native peptides backbone (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body, more capable of penetrating into cells improving clearance, biodistribution and/or pharmacokinetics. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C.A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated amide bonds (—N(CH₃)—CO—), ester bonds (—C(═O)—O—), ketomethylene bonds (—CO—CH₂—), sulfinylmethylene bonds (—S(═O)—CH₂—), α-aza bonds (—NH—N(R)—CO—), wherein R is any alkyl (e.g., methyl), amine bonds (—CH₂—NH—), sulfide bonds (—CH₂—S—), ethylene bonds (—CH₂—CH₂—), hydroxyethylene bonds (—CH (OH)—CH₂—), thioamide bonds (—CS—NH—), olefinic double bonds (—CH═CH—), fluorinated olefinic double bonds (—CF═CH—), retro amide bonds (—NH—CO—), peptide derivatives (—N(R)—CH₂—CO—), wherein R is the "normal" side chain, naturally present on the carbon atom.

These modifications can occur at any of the bonds along the peptide chain and even at several (e.g. 2-3) bonds at the same time.

Natural aromatic amino acids, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halo-genated derivatives of Phe or O-methyl-Tyr.

The polypeptides of some embodiments of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phospho-threonine; and other unusual amino acids including, but not limited to, 2-aminoadipic acid, hydroxylysine, isodes-mosine, nor-valine, nor-leucine and ornithine. Furthermore, the term "amino acid" includes both D- and L-amino acids (stereoisomers).

Tables 1 and 2 below list naturally occurring amino acids (Table 1), and non-conventional or modified amino acids (e.g., synthetic, Table 2) which can be used with some embodiments of the invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |

TABLE 1-continued

| Amino Acid | Three-Letter Abbreviation | One-letter Symbol |
|---|---|---|
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |

TABLE 1-continued

| Amino Acid | Three-Letter Abbreviation | One-letter Symbol |
|---|---|---|
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |

TABLE 2-continued

| Non-conventional amino acid | Code | Non-conventional amino acid | Code |
|---|---|---|---|
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenylpropyl)glycine | Nbhe | N-(N-(3,3-diphenylpropyl) carbamylmethyl-glycine | Nnbhe |
| 1-carboxy-1-(2,2-diphenyl ethylamino)cyclopropane | Nmbc | 1,2,3,4-tetrahydroisoquinoline-3- carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The amino acids of the polypeptides of some embodiments of the present invention may be substituted either conservatively or non-conservatively.

The term "conservative substitution" as used herein, refers to the replacement of an amino acid present in the native sequence in the polypeptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH [(—CH$_2$)$_5$—COOH]—CO— for aspartic acid. Those non-conservative substitutions which fall under the scope of the present invention are those which still constitute a polypeptide capable of binding SPIKE.

The polypeptides of some embodiments of the invention are preferably utilized in a linear form, although it will be appreciated that in cases where cyclization does not severely interfere with polypeptide characteristics, cyclic forms of the polypeptide can also be utilized.

Since the present peptides are preferably utilized in therapeutics which requires the peptides to be in soluble form, the peptides of some embodiments of the invention preferably include one or more non-natural or natural polar amino acids, including but not limited to serine and threonine which are capable of increasing polypeptide solubility due to their hydroxyl-containing side chain.

Following is a description of amino acid mutations, which may be preferably employed.

As used herein, the phrase "plurality of mutations" refer to 3-20, 3-15, 3-10, 3-8, 3-6, 3-5, 4 or 3 mutations (with respect to the human sequence) which affect the KD of the polypeptide to soluble monomeric ACE2.

According to a specific embodiment, the plurality of mutations refers to 3, 4, 5, 6, 7, 8, 9, 10, 11, 12, 13, 14, 15, 16, 17, 18, 19 or 20 mutations.

As used herein "mutation" refers to any mutation (e.g., amino acid substitution, deletion, insertion). According to a specific embodiment, the mutation is a point mutation. According to a specific embodiment, the mutation is a substitution. The definition of mutation is with reference to SEQ ID NO: 37.

In one embodiment, the modification is at position 358 and at least two additional positions 484, 498 and 501.

In another embodiment, the modification is at each of the positions 358, 484, 498 and 501.

In one alternative, the modification further comprises one at position 460.

An exemplary modification at position 358 comprises a 1358F substitution, an exemplary modification at position 460 comprises a N460K substitution, an exemplary modification at position 484 comprises a E498K substitution, an exemplary modification at position 498 comprises a Q498R substitution, and an exemplary modification at position 501 comprises a N501Y substitution.

Modifications (substitutions) for exemplary polypeptides are detailed herein below:

(i) 1358F, N460K, E484K, S494P, Q498R and N501Y;
   (ii) 1358F, N460K, E484K, Q498R and N501Y;
   (iii) I358F, E484K, Q498R and N501Y;
   (iv) I358F. V445K. N460K, I468T. T470M, S477N, E484K, Q498R and N501Y; or
   (v) I358F. V367W, R408D, K417V, V445K, N460K, I468T. T470M, S477N, E484K, Q498R and N501Y.

Thus, according to a specific embodiment, the polypeptide comprises a sequence as least 90% homologous, at least 91% homologous/identical, at least 92% homologous/identical, at least 93% homologous/identical, at least 94% homologous/identical, at least 95% homologous/identical, at least 96% homologous/identical, at least 97% homologous/identical, at least 98% homologous/identical, at least 99% homologous/identical, 100% homologous/identical to the sequence as set forth in SEQ ID NO: 38 as determined using the Standard protein-protein BLAST [blastp] software of the NCBI, with the restriction that the amino acid at position 358 is F and not replaceable, the amino acid at position 460 is K and not replaceable, the amino acid at position 484 is K and not replaceable, the amino acid at position 494 is P and not replaceable, that the amino acid at position 498 is R and not replaceable, the amino acid at position 501 is Y and not replaceable. This polypeptide is referred to herein as B52.

In another embodiment, the polypeptide comprises a sequence as least 90% homologous, at least 91% homologous/identical, at least 92% homologous/identical, at least 93% homologous/identical, at least 94% homologous/identical, at least 95% homologous/identical, at least 96% homologous/identical, at least 97% homologous/identical, at least 98% homologous/identical, at least 99% homologous/identical, 100% homologous/identical to the sequence as set forth in SEQ ID NO: 39 as determined using the Standard protein-protein BLAST [blastp] software of the NCBI, with the restriction that the amino acid at position 358 is F and not replaceable, the amino acid at position 445 is K and not replaceable, the amino acid at position 460 is K and not replaceable, the amino acid at position 468 is T and not replaceable, the amino acid at position 470 is M and not replaceable, the amino acid at position 477 is N and not replaceable, the amino acid at position 484 is K and not replaceable, the amino acid at position 498 is R and not replaceable, the amino acid at position 501 is Y and not replaceable. This polypeptide is referred to herein as B62.

In another embodiment, the polypeptide comprises a sequence as least 90% homologous, at least 91% homologous/identical, at least 92% homologous/identical, at least 93% homologous/identical, at least 94% homologous/identical, at least 95% homologous/identical, at least 96% homologous/identical, at least 97% homologous/identical, at least 98% homologous/identical, at least 99% homologous/identical, 100% homologous/identical to the sequence as set forth in SEQ ID NO: 40 as determined using the Standard protein-protein BLAST [blastp] software of the NCBI, with the restriction that the amino acid at position 358 is F and not replaceable, the amino acid at position 367 is W and not replaceable, the amino acid at position 408 is D and not replaceable, the amino acid at position 417 is V and not replaceable, the amino acid at position 445 is K and not replaceable, the amino acid at position 460 is K and not replaceable, the amino acid at position 468 is T and not replaceable, the amino acid at position 470 is M and not replaceable, the amino acid at position 477 is N and not replaceable, the amino acid at position 484 is K and not replaceable, the amino acid at position 498 is R and not replaceable, the amino acid at position 501 is Y and not replaceable. This polypeptide is referred to herein as B71.

According to another embodiment, the polypeptide comprises a protecting moiety or a stabilizing moiety.

The term "protecting moiety" refers to any moiety (e.g. chemical moiety) capable of protecting the polypeptide from adverse effects such as proteolysis, degradation or clearance, or alleviating such adverse effects.

The term "stabilizing moiety" refers to any moiety (e.g. chemical moiety) that inhibits or prevents a polypeptide from degradation.

The addition of a protecting moiety or a stabilizing moiety to the polypeptide typically results in masking the charge of the polypeptide terminus, and/or altering chemical features thereof, such as, hydrophobicity, hydrophilicty, reactivity, solubility and the like. Examples of suitable protecting moieties can be found, for example, in Green et al., "Protective Groups in Organic Chemistry", (Wiley, 2.sup.nd ed. 1991) and Harrison et al., "Compendium of Synthetic Organic Methods", Vols. 1-8 (John Wiley and Sons, 1971-1996).

The protecting moiety (or group) or stabilizing moiety (or group) may be added to the N-(amine) terminus and/or the C-(carboxyl) terminus of the polypeptide.

Representative examples of N-terminus protecting/stabilizing moieties include, but are not limited to, formyl, acetyl (also denoted herein as "Ac"), trifluoroacetyl, benzyl, benzyloxycarbonyl (also denoted herein as "CBZ"), tert-butoxycarbonyl (also denoted herein as "BOC"), trimethylsilyl (also denoted "TMS"), 2-trimethylsilyl-ethanesulfonyl (also denoted "SES"), trityl and substituted trityl groups, allyloxycarbonyl, 9-fluorenylmethyloxycarbonyl (also denoted herein as "FMOC"), nitro-veratryloxycarbonyl (also denoted herein as "NVOC"), t-amyloxycarbonyl, adamantyl-oxycarbonyl, and p-methoxybenzyloxycarbonyl, 2-chlorobenzyloxycarbonyl and the like, nitro, tosyl ($CH_3C_6H_4SO_2$-), adamantyloxycarbonyl, 2,2,5,7, 8-pentamethylchroman-6-sulfonyl, 2,3,6-trimethyl-4-methoxyphenylsulfonyl, t-butyl benzyl (also denoted herein as "BZL") or substituted BZL, such as, p-methoxybenzyl, p-nitrobenzyl, p-chlorobenzyl, o-chlorobenzyl, 2,6-dichlorobenzyl, t-butyl, cyclohexyl, cyclopentyl, benzyloxymethyl (also denoted herein as "BOM"), tetrahydropyranyl, chlorobenzyl, 4-bromobenzyl, and 2,6-dichlorobenzyl.

According to one embodiment of the invention, the protecting/stabilizing moiety is an amine protecting moiety.

According to a specific embodiment, the protecting/stabilizing moiety is a terminal cysteine residue.

Representative examples of C-terminus protecting/stabilizing moieties are typically moieties that lead to acylation of the carboxy group at the C-terminus and include, but are not limited to, benzyl and trityl ethers as well as alkyl ethers, tetrahydropyranyl ethers, trialkylsilyl ethers, allyl ethers, monomethoxytrityl and dimethoxytrityl. Alternatively the —COOH group of the C-terminus may be modified to an amide group.

Other modifications of polypeptides include replacement of the amine and/or carboxyl with a different moiety, such as hydroxyl, thiol, halide, alkyl, aryl, alkoxy, aryloxy and the like.

According to a specific embodiment, the protecting/stabilizing moiety is an amide.

According to a specific embodiment, the protecting/stabilizing moiety is a terminal cysteine residue.

According to one embodiment, the protecting/stabilizing moiety comprises at least one, two, three or more cysteine residues at the N- or C-termini of the polypeptide.

Also included in the scope of the present invention are "chemical derivative" of a polypeptide or analog. Such chemical derivates contain additional chemical moieties not normally a part of the polypeptide. Covalent modifications of the polypeptide are included within the scope of this invention. Such modifications may be introduced into the molecule by reacting targeted amino acid residues of the polypeptide with an organic derivatizing agent that is capable of reacting with selected side chains or terminal residues. Many such chemical derivatives and methods for making them are well known in the art, some are discussed hereinbelow.

Also included in the scope of the invention are salts of the polypeptides and analogs of the invention. As used herein, the term "salts" refers to both salts of carboxyl groups and to acid addition salts of amino groups of the polypeptide molecule. Salts of a carboxyl group may be formed by means known in the art and include inorganic salts, for example, sodium, calcium, ammonium, ferric or zinc salts, and the like, and salts with organic bases such as those formed for example, with amines, such as triethanolamine, arginine, or lysine, piperidine, procaine, and the like. Acid addition salts include, for example, salts with mineral acids such as, for example, hydrochloric acid or sulfuric acid, and salts with organic acids, such as, for example, acetic acid or oxalic acid. Such chemical derivatives and salts are preferably used to modify the pharmaceutical properties of the polypeptide insofar as stability, solubility, etc., are concerned.

According to one embodiment of the invention, the isolated polypeptide capable of binding soluble ACE2 (i.e., the polypeptide described herein) is attached to a heterologous moiety.

As used herein the phrase "heterologous moiety" refers to an amino acid sequence which does not endogenously form a part of the isolated polypeptide's amino acid sequence. Preferably, the heterologous moiety does not affect the biological activity of the isolated polypeptide (e.g. capability of binding ACE2).

The heterologous moiety may thus serve to ensure stability of the isolated polypeptide of the present invention without compromising its activity. For example, the heterologous polypeptide may increase the half-life of the isolated polypeptide or molecule in the serum.

The heterologous moiety of the present invention may be capable of inducing an antibody dependent cellular-mediated cytotoxicity (ADCC) response.

According to one embodiment, the heterologous moiety does not induce an immune response. Thus, for instance, in the case of Ig, it may contain human sequences that do not produce an immune response in a subject administered therewith.

According to one embodiment, the heterologous moiety is for increasing avidity of the polypeptide.

According to one embodiment, the heterologous moiety is for multimerization of the isolated polypeptide (e.g. at least for dimerization of the isolated polypeptides), as further discussed herein below.

According to one embodiment, the heterologous moiety is a proteinaceous moiety.

Examples of heterologous amino acid sequences that may be used in accordance with the teachings of the present invention include, but are not limited to, immunoglobulin, galactosidase, glucuronidase, glutathione-S-transferase (GST), carboxy terminal polypeptide (CTP) from chorionic gonadotrophin (CGb) and chloramphenicol acetyltransferase (CAT) [see for example U.S. Publication No. 20030171551].

According to a specific embodiment, the heterologous amino acid sequence is an immunoglobulin.

Generally the heterologous amino acid sequence is localized at the amino- or carboxyl-terminus (N-ter or C-ter, respectively) of the isolated polypeptide of the present invention. The heterologous amino acid sequence may be attached to the isolated polypeptide amino acid sequence by any of polypeptide or non-polypeptide bond. Attachment of the isolated polypeptide amino acid sequence to the heterologous amino acid sequence may be effected by direct covalent bonding (polypeptide bond or a substituted polypeptide bond) or indirect binding such as by the use of a linker having functional groups. Functional groups include, without limitation, a free carboxylic acid (C(=O)OH), a free amino group ($NH_2$), an ester group (C(=O)OR, where R is alkyl, cycloalkyl or aryl), an acyl halide group (C(=O) A, where A is fluoride, chloride, bromide or iodide), a halide (fluoride, chloride, bromide or iodide), a hydroxyl group (OH), a thiol group (SH), a nitrile group (C≡N), a free C-carbamic group (NR"—C(=O)—OR', where each of R' and R" is independently hydrogen, alkyl, cycloalkyl or aryl).

An example of a heterologous amino acid sequence which may be used in accordance with this aspect of the present invention is an immunoglobulin amino acid sequence, such as the hinge and Fc regions of an immunoglobulin heavy domain (see U.S. Pat. No. 6,777,196). The immunoglobulin moiety in the molecules of this aspect of the present invention may be obtained from IgG1, IgG2, IgG3 or IgG4 subtypes, IgA, IgE, IgD or IgM.

The polypeptides of the present invention can be generated using recombinant techniques such as described by Bitter et al. (1987) Methods in Enzymol. 153:516-544; Studier et al. (1990) Methods in Enzymol. 185:60-89; Brisson et al. (1984) Nature 310:511-514; Takamatsu et al. (1987) EMBO J. 6:307-311; Coruzzi et al. (1984) EMBO J. 3:1671-1680; Brogli et al. (1984) Science 224:838-843; Gurley et al. (1986) Mol. Cell. Biol. 6:559-565 and Weissbach & Weissbach, 1988, Methods for Plant Molecular Biology, Academic Press, NY, Section VIII, pp 421-463.

The heterologous moiety may also be chemically linked to the isolated polypeptide following the independent generation of each. Thus, the two polypeptides may be covalently or non-covalently linked using any linking or binding method and/or any suitable chemical linker known in the art. Such linkage can be direct or indirect, as by means of a polypeptide bond or via covalent bonding to an intervening linker element, such as a linker polypeptide or other chemical moiety, such as an organic polymer. Such chimeric peptides may be linked via bonding at the carboxy (C) or amino (N) termini of the peptides, or via bonding to internal chemical groups such as straight, branched, or cyclic side chains, internal carbon or nitrogen atoms, and the like. The exact type and chemical nature of such cross-linkers and cross linking methods is preferably adapted to the type and nature of the peptides used.

Thus, the polypeptide of this aspect of the present invention may comprise a heterologous moiety, as described above. Additionally or alternatively, the polypeptide amino acid sequence of the present invention may be attached to a non-proteinaceous moiety.

The phrase "non-proteinaceous moiety" as used herein refers to a molecule, not including polypeptide bonded amino acids, that is attached to the above-described isolated polypeptide's amino acid sequence.

According to one embodiment, the non-proteinaceous moiety is non-toxic.

Exemplary non-proteinaceous moieties which may be used according to the present teachings include, but are not limited to, polyethylene glycol (PEG), Polyvinyl pyrrolidone (PVP), poly(styrene comaleic anhydride)(SMA), and divinyl ether and maleic anhydride copolymer (DIVEMA).

Such a molecule is highly stable (resistant to in-vivo proteolytic activity probably due to steric hindrance conferred by the non-proteinaceous moiety) and may be produced using common solid phase synthesis methods which are inexpensive and highly efficient, as further described hereinbelow. However, it will be appreciated that recombinant techniques may still be used, whereby the recombinant polypeptide product is subjected to in-vitro modification (e.g., PEGylation as further described hereinbelow).

Bioconjugation of non-proteinaceous moieties (such as PEGylation) can confer the isolated polypeptide's with stability (e.g., against protease activities) and/or solubility (e.g., within a biological fluid such as blood, digestive fluid) while preserving its biological activity and prolonging its half-life.

Bioconjugation is advantageous particularly in cases of therapeutic proteins which exhibit short half-life and rapid clearance from the blood. The increased half-lives of bioconjugated proteins in the plasma results from increased size of protein conjugates (which limits their glomerular filtration) and decreased proteolysis due to polymer steric hindrance. Generally, the more polymer chains attached per polypeptide, the greater the extension of half-life. However, measures are taken not to reduce the specific activity of the isolated polypeptide or fusion protein of the present invention (e.g. capability of binding ACE2).

Bioconjugation of the isolated polypeptide's amino acid sequence with PEG (i.e., PEGylation) can be effected using PEG derivatives such as N-hydroxysuccinimide (NHS) esters of PEG carboxylic acids, monomethoxyPEG$_2$-NHS, succinimidyl ester of carboxymethylated PEG (SCM-PEG), benzotriazole carbonate derivatives of PEG, glycidyl ethers of PEG, PEG p-nitrophenyl carbonates (PEG-NPC, such as methoxy PEG-NPC), PEG aldehydes, PEG-orthopyridyl-disulfide, carbonyldimidazol-activated PEGs, PEG-thiol, PEG-maleimide. Such PEG derivatives are commercially available at various molecular weights [See, e.g., Catalog, Polyethylene Glycol and Derivatives, 2000 (Shearwater Polymers, Inc., Huntsville, Ala.)]. If desired, many of the above derivatives are available in a monofunctional monomethoxyPEG (mPEG) form.

In general, the PEG added to the isolated polypeptide's amino acid sequence of the present invention should range from a molecular weight (MW) of several hundred Daltons to about 100 kDa (e.g., between 3-30 kDa). Larger MW PEG may be used, but may result in some loss of yield of PEGylated peptides. The purity of larger PEG molecules should be also watched, as it may be difficult to obtain larger MW PEG of purity as high as that obtainable for lower MW PEG. It is preferable to use PEG of at least 85% purity, and more preferably of at least 90% purity, 95% purity, or higher PEGylation of molecules is further discussed in, e.g., Hermanson, Bioconjugate Techniques, Academic Press San Diego, Calif. (1996), at Chapter 15 and in Zalipsky et al., "Succinimidyl Carbonates of Polyethylene Glycol," in Dunn and Ottenbrite, eds., Polymeric Drugs and Drug Delivery Systems, American Chemical Society, Washington, D.C. (1991).

Conveniently, PEG can be attached to a chosen position in the isolated polypeptide's amino acid sequence by site-specific mutagenesis as long as the activity of the conjugate is retained (e.g. capability of binding ACE2). A target for PEGylation could be any Cysteine residue at the N-terminus or the C-terminus of the isolated polypeptide's amino acid sequence. Additionally or alternatively, other Cysteine residues can be added to the isolated polypeptide's amino acid sequence (e.g., at the N-terminus or the C-terminus) to thereby serve as a target for PEGylation. Computational analysis may be effected to select a preferred position for mutagenesis without compromising the activity.

Various conjugation chemistries of activated PEG such as PEG-maleimide, PEG-vinylsulfone (VS), PEG-acrylate (AC), PEG-orthopyridyl disulfide can be employed. Methods of preparing activated PEG molecules are known in the arts. For example, PEG-VS can be prepared under argon by reacting a dichloromethane (DCM) solution of the PEG-OH with NaH and then with di-vinylsulfone (molar ratios: OH 1: NaH 5: divinyl sulfone 50, at 0.2 gram PEG/mL DCM). PEG-AC is made under argon by reacting a DCM solution of the PEG-OH with acryloyl chloride and triethylamine (molar ratios: OH 1: acryloyl chloride 1.5: triethylamine 2, at 0.2 gram PEG/mL DCM). Such chemical groups can be attached to linearized, 2-arm, 4-arm, or 8-arm PEG molecules.

While conjugation to cysteine residues is one convenient method by which the isolated polypeptide's amino acid of the present invention can be PEGylated, other residues can also be used if desired. For example, acetic anhydride can be used to react with $NH_2$ and SH groups, but not COOH, S—S, or —SCH$_3$ groups, while hydrogen peroxide can be used to react with —SH and —SCH$_3$ groups, but not $NH_2$. Reactions can be conducted under conditions appropriate for conjugation to a desired residue in the polypeptide employing chemistries exploiting well-established reactivities.

For bioconjugation of the isolated polypeptide's amino acid sequence of the present invention with PVP, the terminal COOH-bearing PVP is synthesized from N-vinyl-2-pyrrolidone by radical polymerization in dimethyl formamide with the aid of 4,4'-azobis-(4-cyanovaleric acid) as a radical initiator, and 3-mercaptopropionic acid as a chain transfer agent. Resultant PVPs with an average molecular weight of Mr 6,000 can be separated and purified by high-performance liquid chromatography and the terminal COOH group of synthetic PVP is activated by the N-hydroxysuccinimide/dicyclohexyl carbodiimide method. The isolated polypeptide's or fusion protein's amino acid sequence is reacted with a 60-fold molar excess of activated PVP and the reaction is stopped with amino caploic acid (5-fold molar excess against activated PVP), essentially as described in Haruhiko Kamada, et al., 2000, Cancer Research 60:6416-6420, which is fully incorporated herein by reference.

Resultant conjugated isolated polypeptide (e.g., PEGy-lated or PVP-conjugated isolated polypeptide) are separated, purified and qualified using e.g., high-performance liquid chromatography (HPLC). In addition, purified conjugated molecules of this aspect of the present invention may be further qualified using e.g., in vitro assays in which the binding specificity of isolated polypeptide to its ligand (e.g., ACE2) is tested in the presence or absence of the isolated polypeptide, essentially as described for other polypeptides e.g. by surface plasmon resonance assay or by yeast display assay.

Molecules of this aspect of present invention can be biochemically synthesized such as by using standard solid phase techniques. These methods include exclusive solid phase synthesis, partial solid phase synthesis methods, fragment condensation and classical solution synthesis. These methods are preferably used when the polypeptide is relatively short (i.e., 10 kDa) and/or when it cannot be produced by recombinant techniques (i.e., not encoded by a nucleic acid sequence) and therefore involve different chemistry.

Thus, the polypeptides of some embodiments of the invention may be synthesized by any techniques that are known to those skilled in the art of polypeptide synthesis. For solid phase polypeptide synthesis, a summary of the many techniques may be found in J. M. Stewart and J. D. Young, Solid Phase Polypeptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing polypeptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage.

The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of polypeptide synthesis is disclosed in U.S. Pat. No. 6,472,505.

A particular method of preparing the polypeptide compounds of some embodiments of the invention involves solid phase polypeptide synthesis.

Large scale polypeptide synthesis is described by Andersson Biopolymers 2000; 55 (3): 227-50.

Synthetic polypeptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the polypeptides of the present invention are desired, the polypeptides of the present invention can be generated using recombinant techniques such as described by Bitter et al. (1987) Methods in Enzymol. 153:516-544; Studier et al. (1990) Methods in Enzymol. 185:60-89; Brisson et al. (1984) Nature 310:511-514; Takamatsu et al. (1987) EMBO J. 6:307-311; Coruzzi et al. (1984) EMBO J. 3:1671-1680; Brogli et al. (1984) Science 224:838-843; Gurley et al. (1986) Mol. Cell. Biol. 6:559-565 and Weissbach & Weissbach, 1988, Methods for Plant Molecular Biology, Academic Press, NY, Section VIII, pp 421-463.

For example, a nucleic acid sequence encoding an isolated polypeptide of the present invention (e.g., the amino acid sequences set forth in SEQ ID NOs: 38, 39 or 40) is ligated to a nucleic acid sequence which may include an inframe sequence encoding a proteinaceous moiety such as immunoglobulin.

Exemplary nucleic acid sequences which may be used to express the polypeptides in yeast cells are set forth in SEQ ID NOs: 46, 47 or 48.

Also provided is an expression vector, comprising the isolated polynucleotide of some embodiments of the invention. According to one embodiment, the polynucleotide sequence is operably linked to a cis-acting regulatory element.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion from a host cell in which it is placed. Preferably the signal sequence for this purpose is a mammalian signal sequence.

Preferably, the promoter utilized by the nucleic acid construct of some embodiments of the invention is active in the specific cell population transformed.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Also provided are cells which comprise the polynucleotides/expression vectors as described herein.

Suitable host cells for cloning or expression include prokaryotic or eukaryotic cells. Sec e.g. Charlton, Methods in Molecular Biology, Vol. 248 (B. K. C. Lo, ed., Humana Press, Totowa, N. J., 2003), pp. 245-254, describing expression of antibody fragments in *E. coli*; see Gerngross, Nat. Biotech. 22:1409-1414 (2004), and Li et al., Nat. Biotech. 24:210-215 (2006) for suitable fungi and yeast strains; and see e.g., U.S. Pat. Nos. 5,959,177, 6,040,498, 6,420,548, 7,125,978, and 6,417,429 for suitable plant cell cultures which can also be utilized as hosts.

After expression, the isolated polypeptide may be isolated from the cells in a soluble fraction and can be further purified.

Recovery of the isolated polypeptide may be effected following an appropriate time in culture. The phrase "recovering the recombinant polypeptide or fusion protein" refers to collecting the whole fermentation medium containing the polypeptide or fusion protein and need not imply additional steps of separation or purification.

Notwithstanding the above, proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Molecules of the present invention are preferably retrieved in "substantially pure" form. As used herein, "substantially pure" refers to a purity that allows for the effective use of the protein in the applications, described herein.

Once polypeptides are obtained, they may be tested for binding affinity as discussed in detail above.

It will be appreciated that the vaccine may comprise mRNA which encodes the polypeptides described herein. The mRNA may be formulated for inhalation directly into the lungs. As the delivered mRNA is translated into protein over an extended time, transfected cells will provide prolonged protection against SARS-COV-2 infection both for themselves and neighboring cells for a prolonged time.

To facilitate the uptake of RNA by target cells and to protect RNA from premature degradation, the mRNA may be delivered by one of the following procedures, or any other, in combination with nebulization. By: lipid-based systems, natural or synthetic polymers system, peptide based delivery system, hybrid delivery system or by exosomes. Additional information regarding mRNA delivery is found in Michael Y. T. Chow, Yingshan Qiu, and Jenny K. W. Lam Inhaled RNA Therapy: From Promise to Reality. (2020) Advances in Drug Delivery Systems 41 (10) 715-729.

According to one embodiment, the polypeptides of some embodiments of the invention is also selected capable of neutralizing the Coronaviruses for maximizing therapeutic efficacy.

The term "neutralizing" refers to the ability of the isolated polypeptides to block the site(s) on target cells, thereby blocking the entry of a virus. According to one embodiment, the isolated polypeptides of some embodiments of the invention are capable of neutralizing the virus infectivity by at least 10%, 20%, 30%, 40%, 50%, 60%, 70%, 80%, 90%, or by 100% as compared to infectivity in the absence of the isolated polypeptides of the invention.

Determination of neutralizing of coronaviruses can be carried out using any method known in the art, such as, by in vitro neutralization assays.

According to one embodiment, the isolated polypeptides of the invention are typically capable of retarding or stopping virus replication.

According to one embodiment, the isolated polypeptides are also selected thermo-stable (e.g. stable up to 45° C., up to 50° C., up to 55° C., up to 60° C., or even up to 65° C.). Such determinations can be carried out using any method known in the art, such as by circular dichroism measurements.

Figure 5:
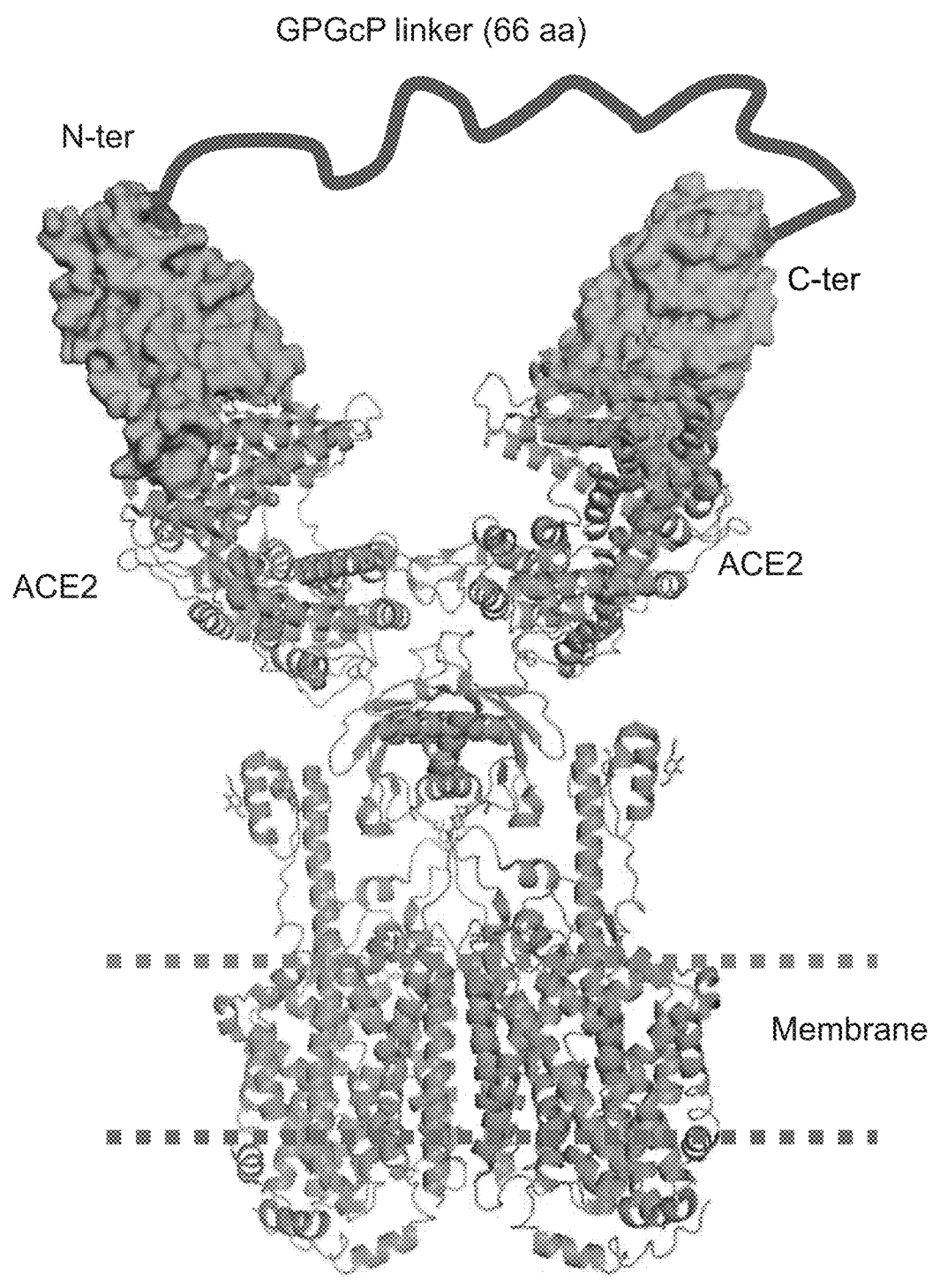
FIG. 5 is an illustration of the 3D structure of a dimer capable of blocking ACE2 according to embodiments of the present invention.

The PDB structure of the ACE2-BOAT1 complex suggest that the ACE2 is anchored on the membrane as a dimer. Thus, the present inventors contemplate engineering a RBD dimer, which will bind both ACE2 subunits, and thus enhances the binding further through the avidity effect (see FIG. 5).

Thus, according to another aspect of the present invention, there is provided a dimer comprising two monomers linked by a linker, wherein each of said two monomers comprises an amino acid sequence encoding SARS COV-2 receptor-binding domain (RBD), wherein each of said monomers binds soluble, monomeric angiotensin-converting enzyme 2 receptor when expressed on the surface of yeast cells with at least 50 fold higher affinity than the wild-type RBD having an amino acid sequence as set forth in SEQ ID NO: 45, when assayed under identical conditions.

In some embodiments, the dimer is such that the amino acid sequence of each of its monomers are the same, thus forming a homodimeric peptide.

In some embodiments, the dimer is such that the amino acid sequence of each of its peptide monomers are different, thus forming a heterodimeric peptide.

As mentioned, the monomers of the dimer of this aspect of the present invention are derived from the SARS COV-2 receptor binding domain. In a particular embodiment, the monomers comprise the mutations described herein above (for example the replacement at position 358-I358F).

According to a specific embodiment, the first and second monomer of the dimer comprises a sequence as least 90% homologous, at least 91% homologous/identical, at least 92% homologous/identical, at least 93% homologous/identical, at least 94% homologous/identical, at least 95% homologous/identical, at least 96% homologous/identical, at least 97% homologous/identical, at least 98% homologous/identical, at least 99% homologous/identical, 100% homologous/identical to the sequence as set forth in SEQ ID NO: 38 as determined using the Standard protein-protein BLAST [blastp] software of the NCBI, with the restriction that the amino acid at position 358 is F and not replaceable, the amino acid at position 460 is K and not replaceable, the amino acid at position 484 is K and not replaceable, the amino acid at position 494 is P and not replaceable, that the amino acid at position 498 is R and not replaceable, the amino acid at position 501 is Y and not replaceable. This polypeptide is referred to herein as B52.

In another embodiment, the first and second monomer of the dimer comprises a sequence as least 90% homologous, at least 91% homologous/identical, at least 92% homologous/identical, at least 93% homologous/identical, at least 94% homologous/identical, at least 95% homologous/identical, at least 96% homologous/identical, at least 97% homologous/identical, at least 98% homologous/identical, at least 99% homologous/identical, 100% homologous/identical to the sequence as set forth in SEQ ID NO: 39 as determined using the Standard protein-protein BLAST [blastp] software of the NCBI, with the restriction that the amino acid at position 358 is F and not replaceable, the amino acid at position 445 is K and not replaceable, the amino acid at position 460 is K and not replaceable, the amino acid at position 468 is T and not replaceable, the amino acid at position 470 is M and not replaceable, the amino acid at position 477 is N and not replaceable, the amino acid at position 484 is K and not replaceable, the amino acid at position 498 is R and not replaceable, the amino acid at position 501 is Y and not replaceable. This polypeptide is referred to herein as B62.

In another embodiment, the first and second monomer of the dimer comprises a sequence as least 90% homologous, at least 91% homologous/identical, at least 92% homologous/identical, at least 93% homologous/identical, at least 94% homologous/identical, at least 95% homologous/identical, at least 96% homologous/identical, at least 97% homologous/identical, at least 98% homologous/identical, at least 99% homologous/identical, 100% homologous/identical to the sequence as set forth in SEQ ID NO: 40 as determined using the Standard protein-protein BLAST [blastp] software of the NCBI, with the restriction that the amino acid at position 358 is F and not replaceable, the amino acid at position 367 is W and not replaceable, the amino acid at position 408 is D and not replaceable, the amino acid at position 417 is V and not replaceable, the amino acid at position 445 is K and not replaceable, the amino acid at position 460 is K and not replaceable, the amino acid at position 468 is T and not replaceable, the amino acid at position 470 is M and not replaceable, the amino acid at position 477 is N and not replaceable, the amino acid at position 484 is K and not replaceable, the amino acid at position 498 is R and not replaceable, the amino acid at position 501 is Y and not replaceable. This polypeptide is referred to herein as B71.

According to another embodiment, the first monomer of the dimer is B52 (or homologs thereof, as defined herein above) and the second is B62 (or homologs thereof, as defined herein above).

According to another embodiment, the first monomer of the dimer is B52 (or homologs thereof, as defined herein above) and the second is B71 (or homologs thereof, as defined herein above).

According to another embodiment, the first monomer of the dimer is B62 (or homologs thereof, as defined herein above) and the second is B71 (or homologs thereof, as defined herein above).

According to a specific embodiment, the dimer comprises an amino acid sequence at least 95% identical/homologous to SEQ ID NO: 43.

Linking of the monomers of the peptide may be effected using any method known in the art provided that the linking does not substantially interfere with the bioactivity of the multimeric peptide—e.g. to interfere with the ability of the dimer to bind to ACE2.

The monomers of this aspect of the present invention may be linked through a linking moiety.

Examples of linking moieties include but are not limited to a simple covalent bond, a flexible peptide linker, a disulfide bridge or a polymer such as polyethylene glycol (PEG). Peptide linkers may be entirely artificial (e.g., comprising 2 to 100 amino acid residues independently selected from the group consisting of glycine, serine, asparagine, threonine, proline, valine and alanine) including their natural posttranslational modification e.g. O- and N-glycosylations or adopted from naturally occurring proteins. Disulfide bridge formation can be achieved, e.g., by addition of cysteine residues, as further described herein below. Linking through polyethylene glycols (PEG) can be achieved by reaction of monomers having free cysteines with multifunctional PEGs, such as linear bis-maleimide PEGs. Alternatively, linking can be performed though the glycans on the monomer after their oxidation to aldehyde form and using multifunctional PEGs containing aldehyde-reactive groups.

Selection of the position of the link between the two monomers should take into account that the link should not substantially interfere with the ability of the dimer to bind to ACE2.

Thus, according to one embodiment the linker comprises the amino acid sequence as set forth in SEQ ID NOs: 41 or 42.

Non-peptide linkers are also possible. For example, alkyl linkers such as —NH—$(CH_2)_s$—C(O)—, wherein s=2-20 could be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. An exemplary non-peptide linker is a PEG linker.

According to another embodiment the link is effected using a coupling agent.

The term "coupling agent", as used herein, refers to a reagent that can catalyze or form a bond between two or more functional groups intra-molecularly, inter-molecularly or both. Coupling agents are widely used to increase polymeric networks and promote crosslinking between polymeric chains, hence, in the context of some embodiments of the present invention, the coupling agent is such that can promote crosslinking between polymeric chains; or such that can promote crosslinking between amino functional groups and carboxylic functional groups, or between other chemically compatible functional groups of polymeric chains. In some embodiments of the present invention the term "coupling agent" may be replaced with the term "crosslinking agent". In some embodiments, one of the polymers serves as the coupling agent and acts as a crosslinking polymer.

By "chemically compatible" it is meant that two or more types of functional groups can react with one another so as to form a bond.

Exemplary functional groups which are typically present in gelatins and alginates include, but are not limited to, amines (mostly primary amines —$NH_2$), carboxyls (—$CO_2H$), sulfhydryls and hydroxyls (—SH and —OH respectively), and carbonyls (—COH aldehydes and —CO-ketones).

Primary amines occur at the N-terminus of polypeptide chains (called the alpha-amine), at the side chain of lysine (Lys, K) residues (the epsilon-amine), as found in gelatin, as well as in various naturally occurring polysaccharides and aminoglycosides. Because of its positive charge at physiologic conditions, primary amines are usually outward-facing (i.e., found on the outer surface) of proteins and other macromolecules; thus, they are usually accessible for conjugation.

Carboxyls occur at the C-terminus of polypeptide chain, at the side chains of aspartic acid (Asp, D) and glutamic acid (Glu, E), as well as in naturally occurring aminoglycosides and polysaccharides such as alginate. Like primary amines, carboxyls are usually on the surface of large polymeric compounds such as proteins and polysaccharides.

Sulfhydryls and hydroxyls occur in the side chain of cysteine (Cys, C) and serine, (Ser, S) respectively. Hydroxyls are abundant in polysaccharides and aminoglycosides.

Carbonyls as ketones or aldehydes can be form in glyco-proteins, glycosides and polysaccharides by various oxidizing processes, synthetic and/or natural.

According to some embodiments of the present invention, the coupling agent can be selected according to the type of functional groups and the nature of the crosslinking bond that can be formed therebetween. For example, carboxyl coupling directly to an amine can be afforded using a carbodiimide type coupling agent, such as EDC; amines may be coupled to carboxyls, carbonyls and other reactive functional groups by N-hydroxysuccinimide esters (NHS-esters), imidoester, PFP-ester or hydroxymethyl phosphine; sulfhydryls may be coupled to carboxyls, carbonyls, amines and other reactive functional groups by maleimide, halo-acetyl(bromo- or iodo-), pyridyldisulfide and vinyl sulfone; aldehydes as in oxidized carbohydrates, may be coupled to other reactive functional groups with hydrazide; and hydroxyl may be coupled to carboxyls, carbonyls, amines and other reactive functional groups with isocyanate.

Hence, suitable coupling agents that can be used in some embodiments of the present invention include, but are not limited to, carbodiimides, NHS-esters, imidoesters, PFP-esters or hydroxymethyl phosphines.

The polypeptides and dimers disclosed herein may be used for treating a Coronavirus infection in a subject in need thereof.

As used herein, "Coronavirus" refers to enveloped positive-stranded RNA viruses that belong to the family Coronaviridae and the order Nidovirales.

Examples of Corona viruses which are contemplated herein include, but are not limited to, 229E, NL63, OC43, and HKU1 with the first two classified as antigenic group 1 and the latter two belonging to group 2, typically leading to an upper respiratory tract infection manifested by common cold symptoms.

However, coronaviruses, which are zoonotic in origin, can evolve into a strain that can infect human beings leading to fatal illness. Thus particular examples of Coronaviruses contemplated herein are SARS-COV, Middle East respiratory syndrome Coronavirus (MERS-CoV), and the recently identified SARS-COV-2 [causing 2019-nCOV (also referred to as "COVID-19")].

It would be appreciated that any coronavirus strain is contemplated herein even though SARS-COV-2 is emphasized in a detailed manner.

According to specific embodiments, the Corona virus is SARS-COV-2.

Exemplary strains of SARS-COV-2 which may be effectively treated include, but are not limited to the Wuhan strain, B.1.1.7, B.1.351 and P.1.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings, male or female, at any age or gender, which suffer from the pathology. Preferably, this term encompasses individuals who are at risk to develop the pathology (e.g., above 65 of age).

The composition of matter comprising the isolated polypeptides or fusion proteins of the present invention can be administered to the subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the composition of matter comprising the isolated polypeptides or fusion proteins accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

According to a particular embodiment, the carrier comprises gelatin (e.g. 1-5 mg/ml of gelatin or 1-3 mg/ml of gelatin or about 2 mg/ml of gelatin).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intrapulmonary or intraocular injections.

Alternately, one may administer the pharmaceutical composition in a local rather than systemic manner, for example, via inhalation into the lungs of the subject.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (composition of matter comprising the isolated polypeptides or fusion proteins) effective to prevent, alleviate or ameliorate symptoms of a disorder (e.g., Coronaviral infection) or prolong the survival of the subject being treated.

According to an embodiment of the present invention, an effective amount of the composition of matter comprising the isolated polypeptides or dimers of some embodiments of the present invention is an amount selected to neutralize Coronaviruses and/or prevent coronaviruses from entering the lung cells.

Determination of a therapeutically effective amount is well within the capability of those skilled in the art, especially in light of the detailed disclosure provided herein.

For example, any in vivo or in vitro method of evaluating Coronavirus viral load may be employed.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide the active ingredient at a sufficient amount to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The present teachings further envisage treating with other anti-viral drugs or anti-inflammatory drugs or anti-coagulants as separate treatments or in a co-formulation.

Without being limited to COVID-19 but for the sake of example, according to a specific embodiment, the antiviral drug is selected from the group consisting of remdesivir, an interferon, ribavirin, adefovir, tenofovir, acyclovir, brivudin, cidofovir, fomivirsen, foscarnet, ganciclovir, penciclovir, amantadine, rimantadine and zanamivir.

Also contemplated are plasma treatments from infected persons who survived and/or anti-HIV drugs such as lopinavir and ritonavir, as well as chloroquine.

Specific examples for drugs that are routinely used for the treatment of COVID-19 include, but are not limited to, Lopinavir/Ritonavir, Nucleoside analogues, Neuraminidase inhibitors, Remdesivir, polypeptide (EK1), abidol, RNA synthesis inhibitors (such as TDF, 3TC), anti-inflammatory drugs (such as hormones and other molecules), Chinese traditional medicine, such ShuFengJieDu Capsules and Lianhuaqingwen Capsule, could be the drug treatment options for COVID19.

According to a specific embodiment, the anti-inflammatory agent is interferon I.

According to a specific embodiment, the interferon I is IFNβ and/or IFNα2.

In a specific embodiment, the polypeptides are provided together with interferon I in a single composition formulated for inhalation (e.g. nebulized together with gelatin).

It will be appreciated that the polypeptides (including dimers) disclosed herein can be used as a vaccine.

As used herein, the term "vaccine" refers to a pharmaceutical preparation (pharmaceutical composition) or product that upon administration induces an immune response, in particular a cellular immune response, which recognizes and attacks a pathogen or a diseased cell such as a cancer cell. The vaccine of the present invention preferably also includes an adjuvant and an immunologically acceptable carrier.

General methods to prepare immunogenic or vaccine compositions are described in Remington's Pharmaceutical Science; Mack Publishing Company Easton, Pa. (latest edition). To increase immunogenicity, the polypeptides of the present invention may be adsorbed to or conjugated to beads such as latex or gold beads, ISCOMs, and the like. Immunogenic compositions may comprise adjuvants, which are substance that can be added to an immunogen or to a vaccine formulation to enhance the immune-stimulating properties of the immunogenic moiety. Liposomes are also considered to be adjuvants (Gregoriades, G. et al., Immunological Adjuvants and Vaccines, Plenum Press, New York, 1989) Examples of adjuvants or agents that may add to the effectiveness of proteinaceous immunogens include aluminum hydroxide, aluminum phosphate, aluminum potassium sulfate (alum), beryllium sulfate, silica, kaolin, carbon, water-in-oil emulsions, and oil-in-water emulsions. A preferred type of adjuvant is muramyl dipeptide (MDP) and various MDP derivatives and formulations, e.g., N-acetyl-D-glucosaminyl-(.beta. 1-4)-N-acetylmuramyl-L-alanyl-D-isoglutami-ne (GMDP) (Hornung, R L et al. Ther Immunol 1995 2:7-14) or ISAF-1 (5% squalene, 2.5% pluronic L121, 0.2% Tween 80 in phosphate-buffered solution with 0.4 mg of threonyl-muramyl dipeptide; see Kwak, L W et al. (1992) N. Engl. J. Med., 327:1209-1238). Other useful adjuvants are, or are based on, cholera toxin, bacterial endotoxin, lipid X, whole organisms or subcellular fractions of the bacteria *Propionobacterium acnes* or *Bordetella pertussis*, polyribonucleotides, sodium alginate, lanolin, lysolecithin, vitamin A, saponin and saponin derivatives such as QS21 (White, A. C. et al. (1991) Adv. Exp. Med. Biol., 303:207-210) which is now in use in the clinic (Helling, F et al. (1995) Cancer Res., 55:2783-2788; Davis, T A et al. (1997) Blood, 90:509), levamisole, DEAE-dextran, blocked copolymers or other synthetic adjuvants. A number of adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.), Amphigen (oil-in-water), Alhydrogel (aluminum hydroxide), or a mixture of Amphigen and Alhydrogel. Aluminum is approved for human use.

The present inventors have developed a novel ligand-inducible fluorescent polypeptide which is particularly useful in yeast display assays. The fluorescent polypeptide is based on UnaG, a fluorescent protein from Japanese cel. UnaG belongs to the fatty-acid-binding protein (FABP) family. The protein is induced to fluoresce on addition of bilirubin.

Thus, according to an aspect of the present invention there is provided an isolated polypeptide comprising an amino acid sequence at least 99% identical to the sequence as set forth in SEQ ID NO: 33.

According to still another aspect of the present invention there is provided a fusion protein comprising a yeast anchoring protein fused to a ligand-inducible fluorescent polypeptide.

Where a heterologous amino acid sequence is fused to the ligand-inducible fluorescent polypeptide, this variant is referred to a fusion protein or a chimeric protein.

As used herein, the term "fused" means that at least a protein or polypeptide is physically associated with another protein or polypeptide, which naturally don't form a complex. According to a specific embodiment the fused molecule is a "fusion polypeptide" or "fusion protein", a protein created by joining two or more heterologously related polypeptide sequences together. The fusion polypeptides encompassed in this invention include translation products of a chimeric nucleic acid construct that joins the DNA sequence encoding the ligand-inducible fluorescent polypeptide with the DNA sequence encoding a yeast anchoring peptide to form a single open-reading frame. In other words, a "fusion polypeptide" or "fusion protein" is a recombinant protein of two or more proteins which are joined by a polypeptide bond.

Examples of yeast anchoring proteins are provided herein above.

The fusion protein may be attached to a protein or peptide of interest. Exemplary proteins/peptides of interest are those derived from coronaviruses (such as the RBD) or ACE2 derived proteins.

According to a specific embodiment, the yeast anchoring protein comprises yeast mating agglutinin A binding protein (e.g. Aga2p).

The inventors further contemplate polynucleotides which encode the protein or fusion protein (e.g. having a sequence as set forth in SEQ ID NO: 34), expression constructs comprising the disclosed polynucleotides, and promoters for expression of the polypeptide in a particular cell system (e.g. promoters for expression in yeast cells).

As mentioned, the fusion proteins disclosed herein may be used to analyze the expression of proteins of interest in cellular systems (e.g. yeast display systems) and for analyzing binding affinity of said proteins of interest.

Thus, according to another aspect of the present invention there is provided a method of analyzing the expression of a protein of interest on the surface of a yeast cell comprising:

(a) transfecting the yeast cell with a polynucleotide encoding the fusion protein described herein under conditions that allows display of said fusion protein on the surface of said yeast cell;

(b) contacting said yeast cell with said ligand so as to induce fluorescence of said fluorescent polypeptide; and (c) analyzing the amount of fluorescence emitted by said fluorescent polypeptide, wherein said amount of fluorescence is indicative of the expression level of the protein of interest.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells-A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H.

Freeman and Co., New York (1980); available immunoassays are extensively described in the patent and scientific literature, see, for example, U.S. Pat. Nos. 3,791,932; 3,839, 153; 3,850,752; 3,850,578; 3,853,987; 3,867,517; 3,879, 262; 3,901,654; 3,935,074; 3,984,533; 3,996,345; 4,034, 074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization-A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

RBD Variants Cloning and Other DNA Manipulations

The RBD domain variants (RBDcon1 AA336-516, RBDcon2 AA336-528, RBDcon3 AA330-528, and RBDcon4 AA319-541) were amplified from mammalian codon optimized SARS-COV-2 Spike protein gene (Sino Biological, SARS-COV-2 (2019-nCOV) Cat: VG40589-UT, GenBank: QHD43416.1) by using PCR (primers Table 3), purified by using NucleoSpin® Gel and PCR Clean-up kit (Nachery-Nagel, Germany) according to manufacturers procedure. Pure amplicons were incorporated in Ndel and BamHI (NEB, USA) cleaved plasmids (pJYDN, pJYDC) via yeast homologous recombination [20].

TABLE 3

| Primer list | | |
|---|---|---|
| Primer name | Purpose | sequence |
| S-CoV_pJYDC_F | Gene amplification with | GGCGGTAGCGGAGGCGGAGGGTCGGCTAGCCATTGCCCTTT TGGTGAAGTTTTTAACG (SEQ ID NO: 1) |
| S-CoV_pJYDC_R | overhangs for recombination with | CTATTACAAGTCCTCTTCAGAAATAAGCTTTTGTTCGGATCC TTCAAAAGAAAGTACTACTACTCTGTATGGTTGG (SEQ ID NO: 2) |
| RBDcon3_pJYDC_F | pJYDC vector | GGCGGTAGCGGAGGCGGAGGGTCGGCTAGCCATCCAAACA TCACCAACCTGTGTC (SEQ ID NO: 3) |
| RBDcon3_pJYDC_R | in yeast | CTATTACAAGTCCTCTTCAGAAATAAGCTTTTGTTCGGATCC CTTTGGTCCACACACTGTGGC (SEQ ID NO: 4) |
| RBDcon4_pJYDC_F | | GGCGGTAGCGGAGGCGGAGGGTCGGCTAGCCATAGGGTCC AACCAACAGAGAG (SEQ ID NO: 5) |
| RBDcon4_pJYDC_R | | CTATTACAAGTCCTCTTCAGAAATAAGCTTTTGTTCGGATCC GAAGTTCACACACTTGTTCTTCACC (SEQ ID NO: 6) |
| S-CoV_pJYDN_F | Gene amplification with | CTGCTTTGGCTGCTCCAGCTAATGGTCATATGTGCCCTTTTG GTGAAGTTTTTAACG (SEQ ID NO: 7) |
| S-CoV_pJYDN_R | overhangs for recombination with pJYDN vector in yeast | GCCCGAACCACCTCCACCAGAGGATCCTTCAAAAGAAAGTA CTACTACTCTGTATGGTTGG (SEQ ID NO: 8) |
| S-CoV_Adap_F | Gene preamplification | TGCCCTTTTGGTGAAGTTTTTAACGCCACCAGGTTTGCCTCT GTC (SEQ ID NO: 9) |
| S-CoV_Adap_R | | TTCAAAAGAAAGTACTACTACTCTGTATGGTTGGTAGCCCA CTCCATTGGTTGG (SEQ ID NO: 10) |
| RBD-bind-F | Primers for | CTACAAACTGCCTGATGACTTCAC (SEQ ID NO: 11) |
| RBD-int_R | sequencing and libraries preparation | GTCCAGGTTGTTGCTGTTCCAG (SEQ ID NO: 12) |
| RBDcon2_pCAGGS_F | Cloning of RBD | CCATGTTCGTGTTTCTGGTGCTGCTGCCTCTGGTGTCCAGCA CCAACCTGTGCCCTTTTGGTGAAGTTTTTAACG (SEQ ID NO: 13) |
| pCA_RBD mut_F | gene in pCAGGS and | CCATGTTCGTGTTTCTGGTGCTGCTGCCTCTGGTGTCCAGCA CCCCAAACATCACCAACCTGTGCCCTTTTGGTGAAGTTTTTA ACG (SEQ ID NO: 14) |
| pCA_RBD mut_R | pHL-sec vectors | CGACTTAAGATCGATGCGGCCGCGAGCTCGAATTTTATCAA TGGTGATGGTGATGGTGCTTTGGTCCACACACTGTGGC (SEQ ID NO: 15) |

TABLE 3-continued

Primer list

| Primer name | Purpose | sequence |
|---|---|---|
| RBD_ N354E_F | Site- directed | CGCCACCAGGTTTGCCTCTGTCTATGCCTGGGAAAGGAAGA GGTTTAGCAACTGTGTG (SEQ ID NO: 16) |
| RBD_ Y36SW_F | mutagenesis of | CAGGAAGAGGTTTAGCAACTGTGTGGCTGACTGGTCTGTGC TCTACAACTCTGCC (SEQ ID NO: 17) |
| RBD_ V367W_F | RBD clone | GAAGAGGTTTAGCAACTGTGTGGCTGACTACTCTTGGCTCT ACAACTCTGCCTCCTTCAG (SEQ ID NO: 18) |
| RBD_ T385R_F | B52 | CTTCAGCACCTTCAAGTGTTATGGAGTGAGCCCACGTAAAC TGAATGACCTGTGTTTCACCAATG (SEQ ID NO: 19) |
| RBD_ R408D_F | | CTGACTCCTTTGTGATTAGGGGAGATGAGGTGGATCAGATT GCCCCTGGACAAACAG (SEQ ID NO: 20) |
| RBD_ Q414A_F | | GGGAGATGAGGTGAGACAGATTGCCCCTGGAGCCACAGGC AAGATTGCTGACTACAAC (SEQ ID NO: 21) |
| RBD_ K417V_F | | GGTGAGACAGATTGCCCCTGGACAAACAGGCGTTATTGCTG ACTACAACTACAAACTGCC (SEQ ID NO: 22) |
| RBD_ Y453F_F | | GACAGCAAGGTGGGAGGCAACTACAACTACCTCTTTAGACT GTTCAGGAAGACAAGC (SEQ ID NO: 23) |
| RBD_ L455R_F | | GGTGGGAGGCAACTACAACTACCTCTACAGACGTTTCAGGA AGAGCAAGCTGAAACC (SEQ ID NO: 24) |
| RBD_ Q493M_F | | GAGTGAAGGGCTTCAACTGTTACTTCCCACTCATGTCCTATG GCTTCCGACCAACC (SEQ ID NO: 25) |
| RBD_E, K484R_F | | CCAGGCTGGCAGCACACCATGTAATGGAGTGCGCGGCTTCA ACTGTTACTTCCCACTC (SEQ ID NO: 26) |
| RBD_Q, R498H_F | | CTGTTACTTCCCACTCCAATCCTATGGCTTCCATCCAACCTA TGGAGTGGGCTACC (SEQ ID NO: 27) |
| RBD_N, Y501F_F | | CTTCCCACTCCAATCCTATGGCTTCCGACCAACCTTTGGAGT GGGCTACCAACCATAC (SEQ ID NO: 28) |
| RBD_ Y505W_F | | CCTATGGCTTCCGACCAACCTATGGAGTGGGCTGGCAACCA TACAGGGTGGTGGTGC (SEQ ID NO: 29) |
| RBD_ L517M_F | | CCAACCATACAGGGTGGTGGTGCTGTCCTTTGAAATGCTCC ATGCCCCTGCCACAGTG (SEQ ID NO: 30) |
| B62_ S694PF | Site- directed | GTGAAGGGCTTCAACTGTTACTTTCCACTCCAACCTTATGGC TTCCGACCAACCTATG (SEQ ID NO: 31) |
| B62_ L455RF | mutagenesis of RBD clone B62 | GCAAGAAGGGAGGCAACTACAACTACCTCTACAGACGTTTC AGGAAGAGCAAACTGAAACCATTTG (SEQ ID NO: 32) |

Insertions of RBD genes into mammalian expression vectors pCAGGS and pHL-sec were done in two steps. Initially, the RBD gene was inserted in helper vector pCA by restriction-free cloning. pCA is a pCAGGS derivative lacking 862 bp in the high GC rich region (nt 672-1534) in chimeric intron sequence therefore enabling restriction cloning. In the second step, the correctly inserted RBDs with flanking sequences were cleaved by using restriction enzymes XbaI and XhoI (NEB, USA) and ligated (T4 DNA ligase, NEB, USA) in cleaved full-length plasmid pCAGGS or pHL-sec.

Site-directed mutagenesis of RBDs was performed by restriction-free cloning procedure described in Tamar Unger et al., paper with primers listed in Table 3. Megaprimers were amplified by KAPA HiFi HotStart ReadyMix (Roche, Switzerland), purified with NucleoSpin™ Gel and PCR Clean-up Kit (Nachery-Nagel, Germany) and subsequently inserted by PCR in the destination using high fidelity Phusion® (NEB, USA) or KAPA polymerases. The parental plasmid molecules were inactivated by DpnI treatment (1 h, NEB, USA) and the crude reaction mixture were transformed to electrocompetent *E. coli* Cloni® 10G cells (Lucigen, USA). The clones were screened by colony PCR and their correctness was verified by sequencing.

Yeast Transformation and Cultivation Procedures

The sequence verified plasmids were transformed into the EBY100 *Saccharomyces cerevisiae* strain and grown on yeast minimal SD-W plates. Single colonies were inoculated into 1.0 ml liquid SD-CAA media (20 g glucose, 6.7 g yeast nitrogen base, 5 g bacto casamino acids, 5.4 g $Na_2HPO_4$, 8.56 g $NaH_2PO_4$ per 1L), and grown overnight at 30° C. (220 rpm). The overnight cultures were spun down (3000 g. 3 min) and the exhausted culture media was removed prior dilution in the expression media SG-CAAr (20 g galactose, 2 g glucose, 8 g yeast nitrogen base, 8 g bacto casamino acids, 5.4 g $Na_2HPO_4$, 8.56 g $NaH_2PO_4$) with an addition of 1 nM DMSO solubilized bilirubin. The expression culture was diluted to the final OD 1 and grown at different temperatures 20, 30, and 37° C. overnight (12-14 hours, 220 rpm). Aliquots of expressed cells (100 µl) were collected by centrifugation (3000 g. 3 min) resuspended in ice cold PBSB buffer (PBS with 1 g/L BSA), passed through cell strainer nylon membrane (40 µM, SPL Life Sciences, Korea) and directly analyzed.

Binding Assays and Binding Curve Determination by Using Yeast Display

Aliquots of expressed cells (106), washed in PBSB buffer, were resuspended in analysis solution across a range of concentrations. The analysis solution consisted of PBSB supplemented with given concentration of ligand—CFR640R succinimidyl ester labeled (Biotium, USA) ACE2 enzyme extracellular portion (AA Q18-S740) and expression labeling reagent. ACE2 enzyme was produced by the Israel Structural proteomic center (ISPC) in HEK293 cells.

For expression labeling, the bilirubin (1 nM final concentration), was added to the analysis solution for pJYDC and pJYDN plasmids to allow for eUnaG2 holoform formation and manifestation of its green/yellow fluorescence (Ex. 498 nm, Em. 527 nm). Correspondingly, the purified ALFA-mNeonGreen protein was added to the mixture (5 nM) in combination with pJYDC3 plasmid which bears its counterpart—DnbALFA nanobody. The volume of labeling solution was adjusted (1-100 ml) to avoid the ligand depletion greater than 10% as well as the time needed to reach the equilibrium (1 h-12 h). Samples were incubated at 4° C. and mixed by using lab rotator (5 rpm). Samples were collected by centrifugation (3000 g. 3 min) before cytometry analyses, resuspended in ice cold PBSB buffer (200 µl), passed through cell strainer and analyzed. The yeast surface expression and binding signals were determined by flow cytometry using BD Accuri™ C6 Flow Cytometer (BD Biosciences, USA) using single cell event gating. Green fluorescence channel (FL1-A) was used to detect RBD expression positive cells (RBD+), and far-red fluorescent channel (FL4-A) recorded CF®640R binding signals (CF640+). Mean CF®640R fluorescence signals of RBD+ cells, subtracted by RBD-population FL4-A signal, were used for determination of binding constant KD. The fitting of standard non-cooperative Hill equation was done via nonlinear least squares regression using Python 3.7. The total concentration of yeast exposed protein was fitted together with two additional parameters describing given titration curve.

DNA Library Preparation

SARS-COV-2 RBD gene (RBD) libraries were prepared by MnCl$_2$ error prone mutagenesis method [22] by using Taq Ready mix (Hylabs, Israel). The mutagenic PCR reactions, prepared in 50 µl, were supplemented with increasing MnCl$_2$ concentration: 0.05, 0.1, 0.2, 0.4, 0.6, 0.8 and 1.0 nM and amplified. Template DNA concentration ranged between 100 and 400 ng per reaction and 25-35 reaction cycles were applied until the good product amplification. The amplified DNA was purified, pooled and used directly for yeast transformation via electroporation.

The whole gene randomization together with flanking was applied for creation of stabilization libraries (nucleotides-152-621). Gene fragment, comprising of nucleotides 260-621, was mutagenized for affinity maturations cycles. The rest of RBD with necessary overlap (1-321) was added by recombination with non-mutagenized PCR product.

Example 1

Development of Yeast Display Methodology to Generate Ultra-Tight Binders

Figure 1:
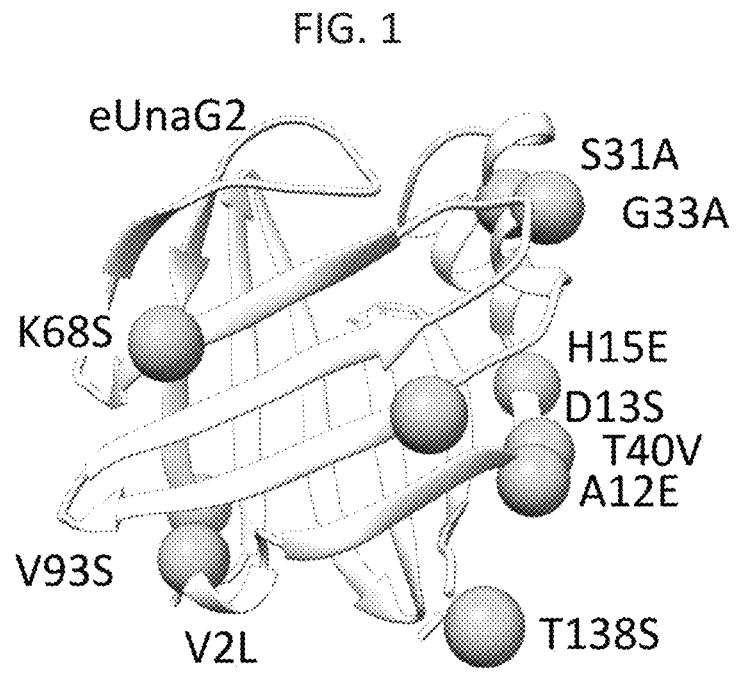

A simple, fast, efficient and reliable antibody-free yeast display platform was developed. Two reporter proteins—cUnaG2 and DnbALFA were tailored, for their use in yeast display. UnaG is a bilirubin dependent green/yellow fluorescence protein naturally identified in Japanese eel (Anguilla *japonica*) and nbALFA is an ALFA-tag binding nanobody [14]. To improve the UnaG protein fluorescence properties and cell surface exposure, computational and experimental procedures were combined. The multiple stabilizing mutations were predicted by consensual design of all available structures using the Pross web-server and further complemented with gain of N-glycosylation mutations [16]. All 15 in silico predicted mutations were used to create a mutation library. Proteins with randomly incorporated stabilizing mutations were displayed on the EBY100 yeast cell surface. Cells associated with stronger fluorescence intensities were isolated by three-rounds of FACS sorting. 10 enhancing mutations were introduced into a single protein, cUnaG2 (FIG. 1) which results in 5-fold increased fluorescence intensity upon addition of bilirubin (which is a cofactor that transforms the apo-UnaG to the fluorescent holo-form) as measured by FACS.

Protein sequence of modified eUnaG2 is set forth in SEQ ID NO: 33.

Nucleic acid sequence of modified eUnaG2 optimized for expression in yeast is set forth in SEQ ID NO: 34.

A similar approach was applied to enhance ALFA-tag binding nanobody. 10 mutations were introduced in nbALFA and a variant DnbALFA showing 10-fold higher expression in *E. coli* and 3-fold higher expression on the surface of yeast compared to wild type was produced. The nanobody was used to bind the purified ALFA-mNeonGreen protein which provides strong green fluorescence for expression detection.

Protein sequence of modified ALFA-tag binding nanobody is set forth in SEQ ID NO: 35.

Nucleic acid sequence of modified ALFA-tag binding nanobody for expression in yeast is set forth in SEQ ID NO: 36.

Engineered reporter proteins together with newly assembled plasmid backbone and optimized spacers gave rise to new yeast display platform consisting of 11 different plasmid modifications. These plasmids allow for N-terminal (pJYDN plasmids) and also C-terminal (pJYDC) fusions with Aga2p enabling expression optimization and different detection strategies.

Example 2

Optimizing RBD Expression, Stability and Binding Affinity Towards ACE2

Selection strategies: Overall, the RBD was subjected to 8 rounds of library constructions on yeast for optimization. Each library was subjected to 3 to 4 consecutive selections on a FACS sorter. In each selection the top 0.1-1% yeast cells with minimum of 20K cells were collected.

3 different strategies were applied for selection: 3 libraries were selected for RBD stability and expression, 4 libraries were constructed for tight ACE2 binding and one library was constructed for selection for fast association between the RBD and ACE2.

First library S1—stability
Second library S2—stability
Third library—B3 binding
Fourth library—B4 binding
Fifth library—B5 binding
Sixth library—B6 binding
Seventh library—Fast association
Eighth library—S3 stability The best variants obtained from yeast display (B52 and B62) were further engineered by site directed mutagenesis to enhance protein stability and binding affinity, as summarized in Table 4.

TABLE 4

| | | | Comparison of different RBD mutants | | |
|---|---|---|---|---|---|
| Clone name | Mutations | Tm [° C.] | ACE2 enzyme activity Inhibition | Yeast display estimated affinity K$_D$ | Binding affinity K$_D$ measured by Biacore S200 |
| RBDcon2 | WT (AA 336-528) | 55.0 | No inhibition | 1.7 ± 0.3 nM | 16 ± 2 nM |

TABLE 4-continued

| | Comparison of different RBD mutants | | | | |
|---|---|---|---|---|---|
| Clone name | Mutations | Tm [° C.] | ACE2 enzyme activity Inhibition | Yeast display estimated affinity $K_D$ | Binding affinity $K_D$ measured by Biacore S200 |
| RBDcon2 B36 | I358F, I468T, N481Y, N501Y | 54.6 | | 268 ± 10 pM | 10 ± 2 nM |
| RBDcon2 B52 | I358F, N460K, E484K, S494P, Q498R, N501Y | 61.9 | No inhibition | 40 ± 16 pM | 240 ± 10 pM |
| RBDcon2 B521 | I358F, N460K, E484K, Q498R, N501Y | 58.2 | | 14 ± 2 pM | 170 ± 10 pM |
| RBDcon2 B55 | I358F, E484K, Q498R, N501Y | 54.8 | | 12.5 ± 0.6 pM | |
| RBDcon2 B62 | I358F, V445K, N460K, I468T, T470M, S477N, E484K, Q498R, N501Y | 57.9 | No inhibition | 2.5 ± 1 pM | 16 ± 2 pM |
| RBDcon2 B71 | I358F, V367W, R408D, K417V, V445K, N460K, I468T, T470M, S477N, E484K, Q498R, N501Y | 63 | No inhibition | 8.5 ± 1 pM | 160 ± 20 pM |

Figure 2:
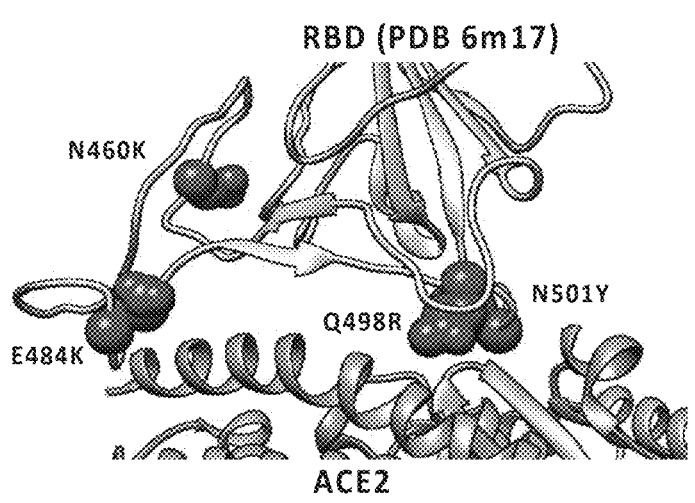
FIG. 2 locations of the manifested mutations in round 5 of the selection on the CoV-2 receptor-binding domain (RBD).
Figures 4A, 4B, 4C, 4D:
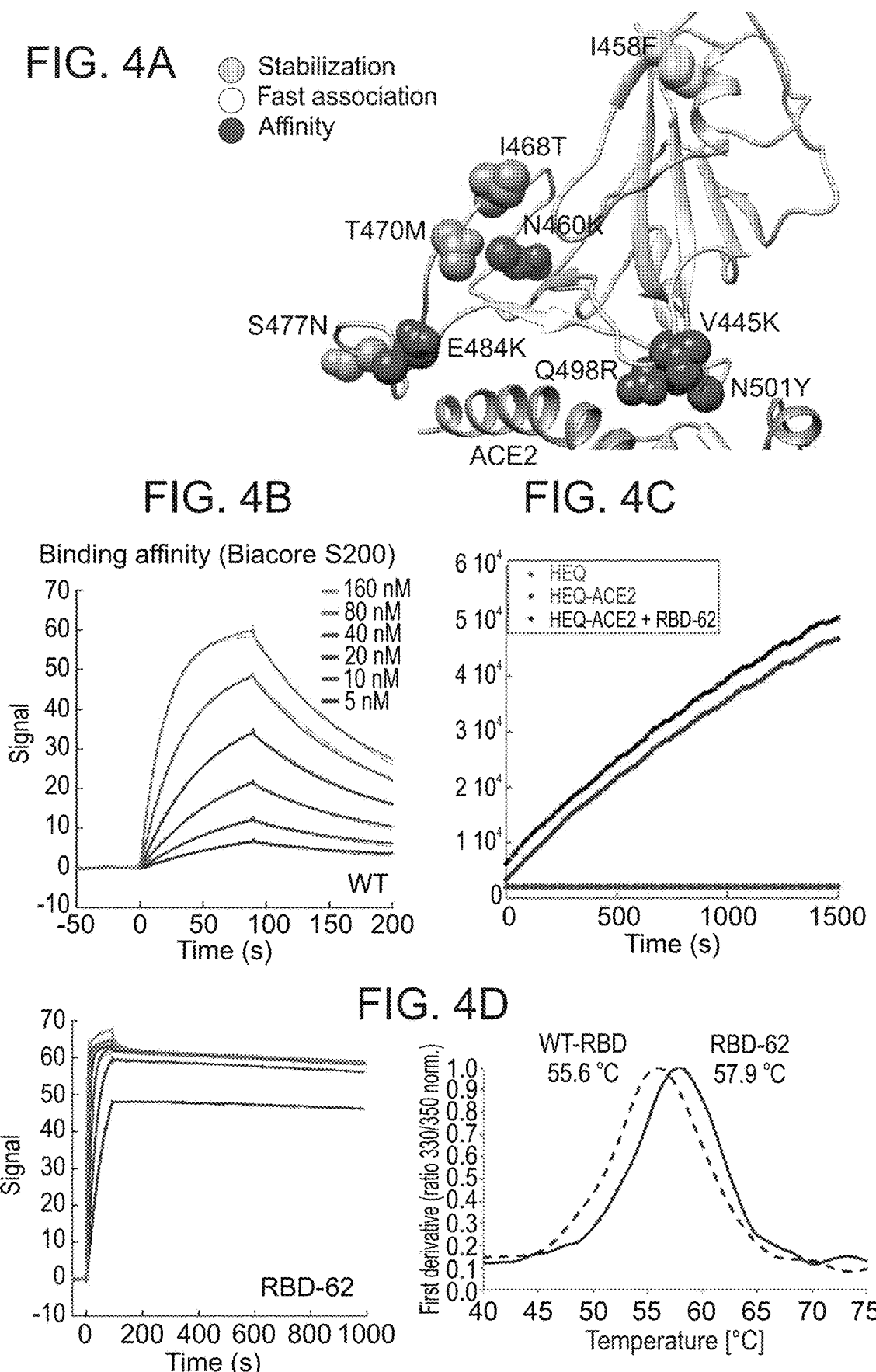
FIGS. 4A-D Comparing wild-type RBD to RBD-62. (A) shows the mutations incorporated in RBD-62 (yellow, red and orange), colored by selection for stability, affinity and fast association respectively. (B) shows the results of SPR Biacore S200 binding sensorgrams for RBD-WT (top) and RBD-62 (bottom) at six concentrations of analyte (5-160 nM). The black line is the global fit using the build-in function, from which binding affinities of 17 nM and 16 pM were calculated respectively. (C) ACE2 activity was determined on ACE2 expressing HEK293 cells using SensoLyte® 390 ACE2 Activity Assay Kit (Fluorimetric), which measures Mc-Ala/Dnp fluorescence resonance energy transfer (FRET) peptide. In the FRET peptide, the fluorescence of Mc-Ala is quenched by Dnp. Upon cleavage into two separate fragments by ACE2, the fluorescence of Mc-Ala is recovered, and can be monitored at excitation/emission=330/390 nm. RBD-62 was added at a concentration of 10 nM (10000-fold the affinity) for 24 hr prior to the ACE2 activity measurement. (D) thermal denaturation of WT-RBD and RBD-62 as determined using a Tycho™ NT.6 Nano-DSF (Nano Temper).

Selected mutations: Stabilization libraries S1 and S2 resulted in the selection the I358F mutation, which nicely fits inside the hydrophobic pocket formed in the RBD domain. This mutation was incorporated in all following libraries. The $3^{rd}$ to $6^{th}$ libraries were used for selection for tighter binding. The most notable mutations that were selected during the process were N460K, E484K, Q498R and N501Y. The locations of these mutations on the RBD structure is shown in FIG. 2. The binding affinity towards ACE2 as measured through expression of the single clones on the yeast surface are given in Table 4. RBD-B36 (from selection 3) showed a 6-fold improvement over WT-RBD. Clones RBD-B52 and RBD-B521 (with one AA difference between the two) bound with an affinity of 40 and 14 pM to ACE2 (Table 4 and FIG. 3A). RBD-B52 was selected for further analysis. RBD-B52 was expressed in HEK293 cells and purified using the fused His-tag. Using the purified protein, ACE2 binding was measured using the Octet RED96 system (FIG. 3B), potential inhibition of ACE2 enzymatic activity (FIG. 3C) and its thermostability (FIG. 3D). While the protein binds to high affinity, is more stable than the WT-RBD and does not inhibit the ACE2 enzymatic activity, its rate of association is somewhat slow (FIG. 3B). Therefore, an additional association selection step was added using yeast display as previously described [17]. This resulted in the selection of further mutations, resulting in the clone RBD-62, which binds ACE2 with an affinity of 2.5 pM (FIG. 3A). FIG. 4A shows the mutations incorporated in RBD-62. The protein was expressed and further analyzed similarly to RBD-52 (FIG. 4B-D). Table 4 provides a summary of the different RBD enhancing mutations and the current knowledge on their effect on stability, level of expression and ACE2 binding.

Fine Tuning for Optimization of the ACE2 RBD Inhibitor

The effect of additional mutations on binding affinity and level of protein expression on the yeast surface is shown in Table 5. Overall, no mutation increased binding. However, three mutations V367W, R408D, and K417V had strong positive effect on protein expression (stability) and were combined together in new clone B71. Yeast display based affinity analysis showed a 2.5-fold reduction in binding affinity accompanied by huge gain in terms of yeast surface expression.

TABLE 5

| | Mutations predicted for stabilization from Starr et al., 2020 [18] | |
|---|---|---|
| RBD-52 mutation | Effect on yeast surface expression | Effect on affinity |
| N354E | – | – – – |
| Y365W | ++ | – |
| V367W | +++ | – |
| R408D | + | – |
| Q414A | ++ | – – |
| K417V | +++ | – |
| L455R | + | – |
| L517M | – | – – – |
| S494P | ++ | – |
| Mutations predicted to be affinity enhancing | | |
| T385R | – | – |
| Y453F | – | – – |
| Q493M | – – | – |
| Ewt, K484R | – | – |
| Qwt, R498H | – – | – |
| Nwt, Y501F | – | – |
| Y505W | – – – | – |
| Mutations tested in combination with RBD-62 | | |
| Y365W | + | – – |
| V367W | +++ | – |
| R408D | + | – |
| Q414A | ++ | – – – |
| K417V | +++ | – |
| L455R | + | – – |
| S494P | + | – – |

Designing a Dual-RBD Binding Domain for Enhanced Binding Avidity

The PDB structure of the ACE2-BOAT1 complex suggest that the ACE2 is anchored on the membrane as a dimer. This opens the possibility of engineering a RBD dimer, that will bind both ACE2 subunits, and thus enhances the binding further trough the avidity effect. The difficulty in this is the large distance between the C-terminus of one RBD and the N-terminus of the second RBD when bound to ACE2. To overcome this problem, a GPGcP linker extended to 66 amino acids, fused to C and N-termini of both RBD-62 and RBD-71 was used.

Example 3

Figure 6A:
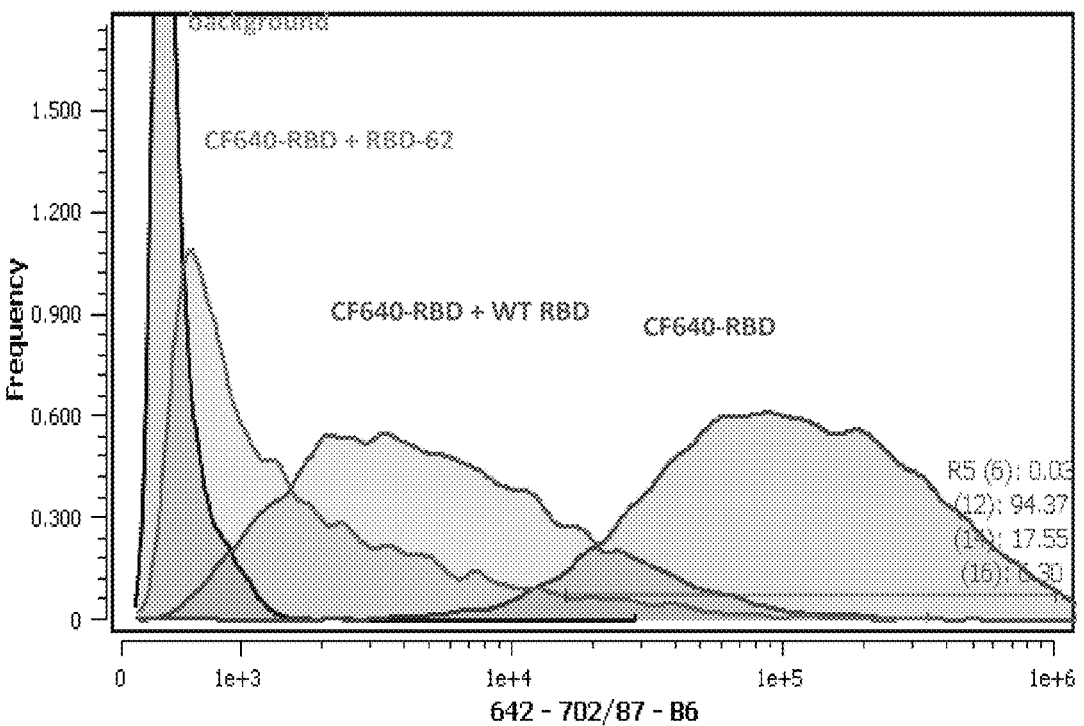
FIGS. 6A-D (A) HEK-ACE2 cells were incubated with labeled (CF640) WT-RBD (blue), and chased with 100 nM WT RBD (red) or 20 nM of RBD-62 (Green line), showing that RBD-62 outcompeted >99% or WT-RBD. (B) HEK-ACE2 cells were incubated with labeled (CF640) WT-RBD (blue) and chased with RBD-62 at concentrations of 2, 4, 8, 12.5 and 20 nM. 4 nM RBD-62 outcompeted the labeled WT-RBD. (C) HEK-ACE2 were pre-incubated with either WT-RBD r RBD-62 at the given concentrations for 1 hr before pseudo-viruses displaying the spike protein of CoV-2 were added. The cells were incubated with the pseudo-viruses for 48 hours before they were evaluated for GFP expression. The pseudovirus used contains the mRNA of GFP, which is the marker of infection. The IC50 for WT RBD was 88 nM and for RBD-62, 5.5 nM. (D) Inhibition of infection of SARS-COV-2-WT, B.1.1.7 (alpha), B.1.351 (beta), and P.1 (gamma) variants to VeroE6 cells by RBD-WT and RBD-62 proteins. Each data point represents the average of 6 repeats, with standard error. The number of viruses was determined by plaque assay (see methods). The curves were fitted to the [agonist] vs response-variable slope function within Prism. The gray zone is below the limit of detection. Fitted IC50 and IC90 values are shown.
Figure 6B:
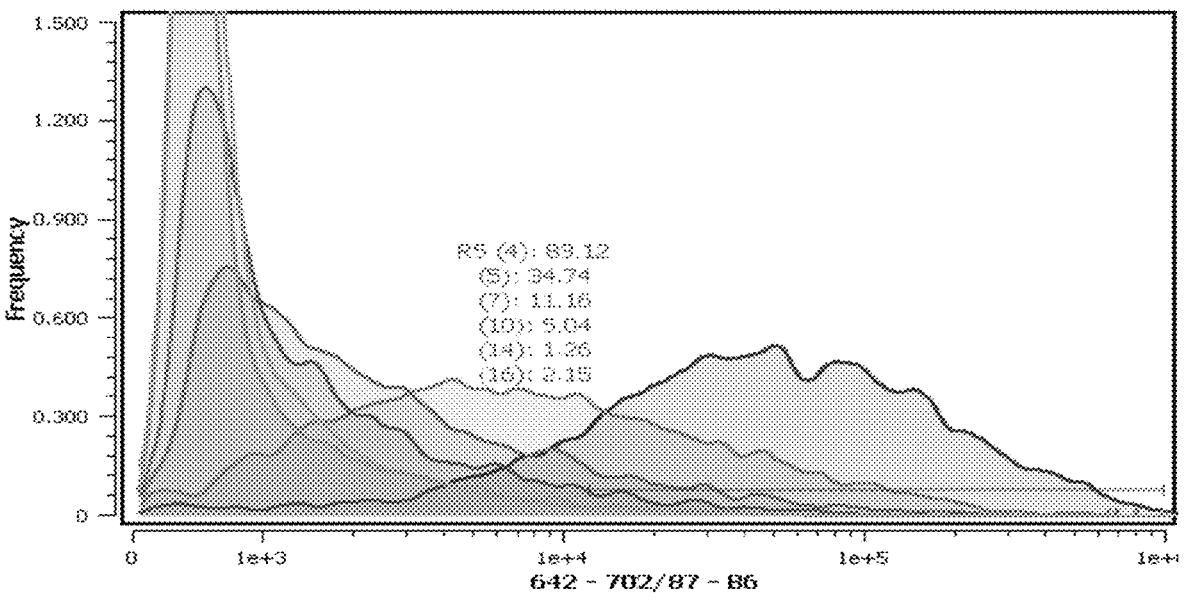
Figure 6C:
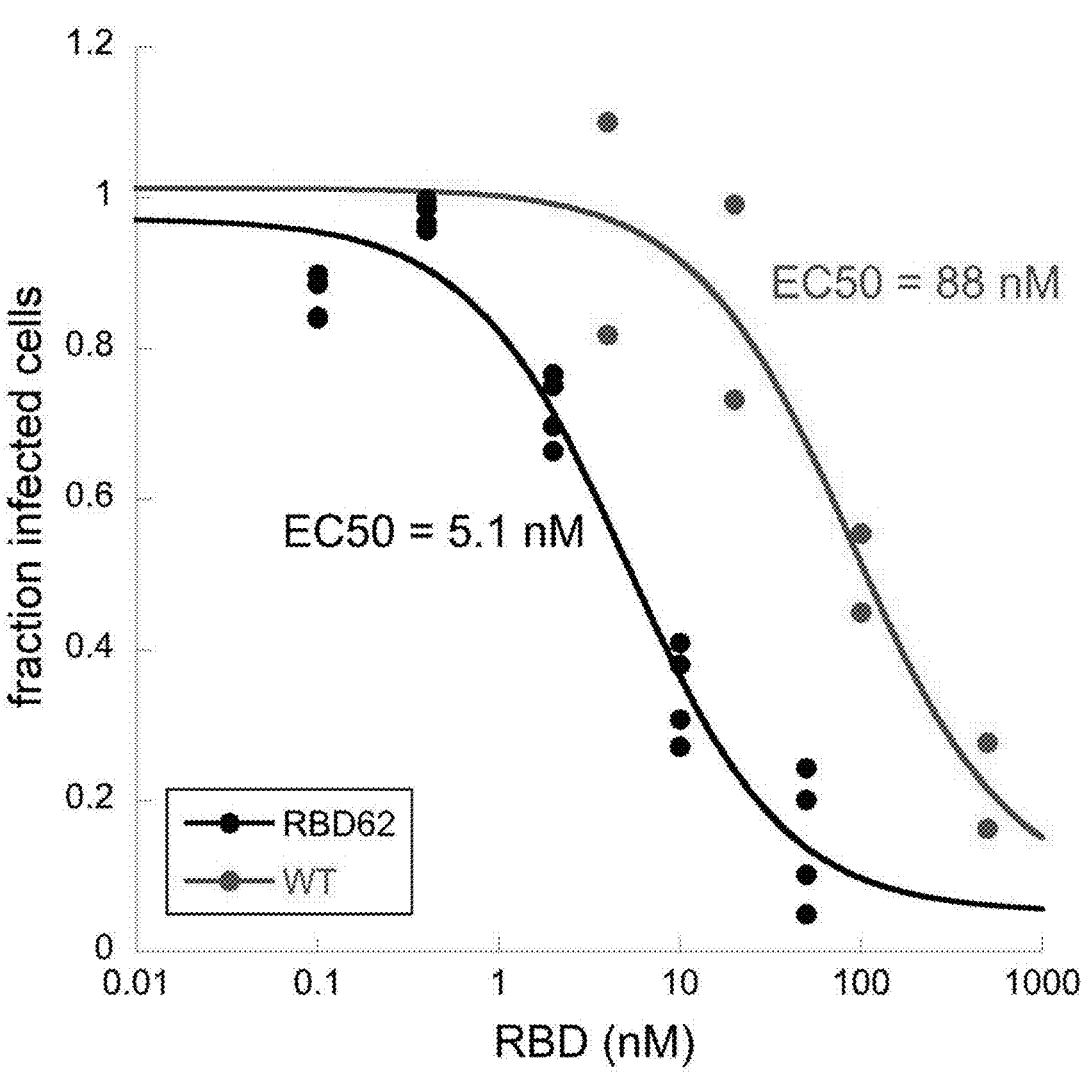
Figure 6D:
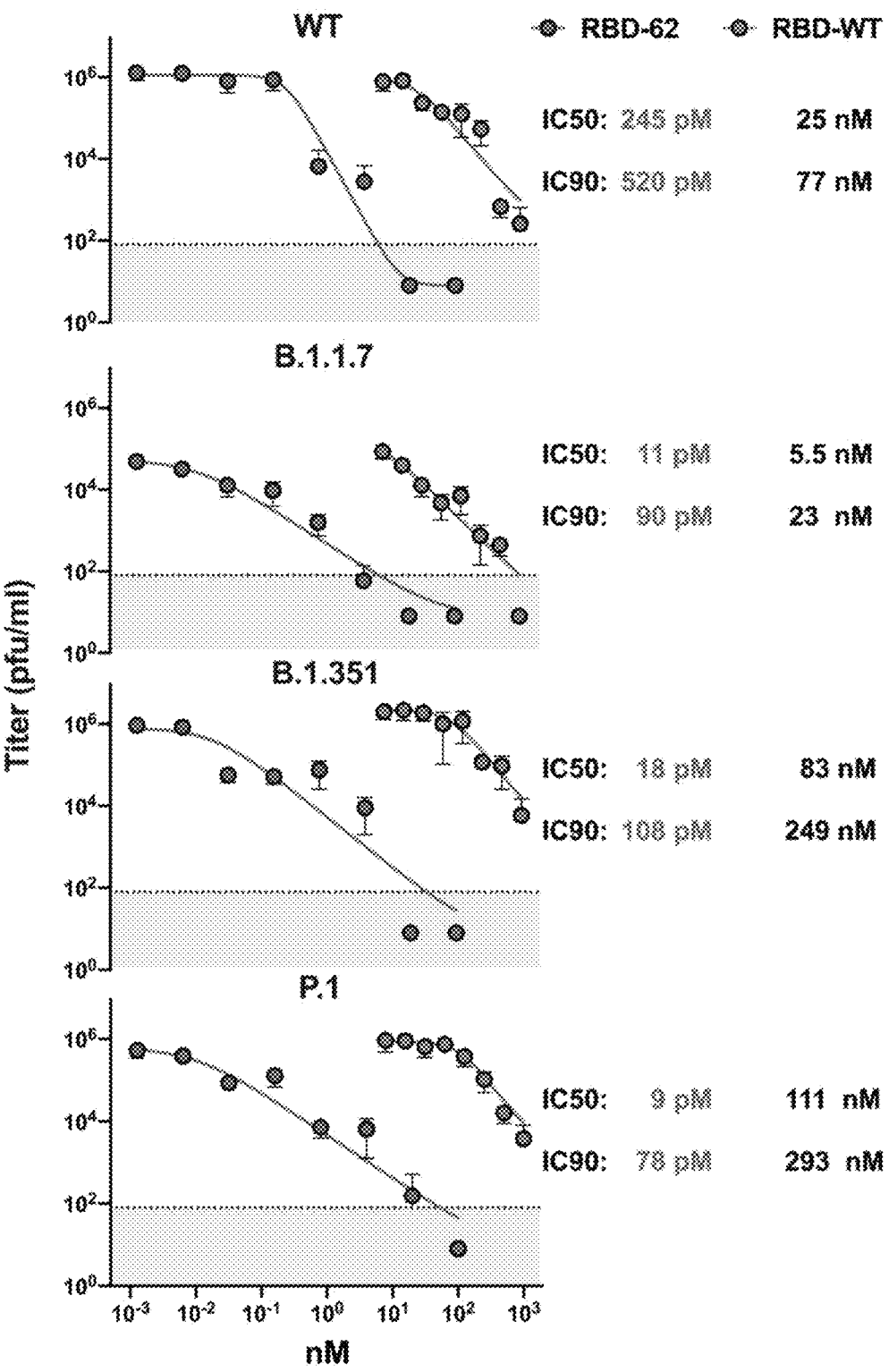

Evaluating the Activity of RBD-62 on Cells in Inhibiting SARS-COV-2 Virus Transfection The ability of RBD-62 to outcompete WT-RBD on HEQ293 cells that express high surface concentrations of ACE2 was tested. FIGS. 6A and B show that low nM concentration of RBD-62 efficiently blocks ~99% of WT-RBD binding (which was color-labeled). Next, pseudo-viruses were used that express the spike protein on their surface, resulting in infection of RNA encoding the GFP gene into cells. The level of GFP with increasing concentrations of either WT-RBD or RBD-62 was monitored. FIG. 6C shows a titration curve of both. The EC50 for WT-RBD was 88 nM, while for RBD-62 it was 5.5 nM. These experiments were done on HEQ cells overexpressing ACE2. Finally, a robotic platform was used to evaluate SARS-COV-2 infection with WT-RBD and RBD-62. VeroE6 cells were incubated with the RBDs, and then challenged with SARS-COV-2 of the WT (Wuhan variant), as well as B.1.1.7 (alpha), B.1.351 (beta) and P.1 (gamma) virus variants. IC50 and IC90 values were 100-1000-fold lower for RBD-62, with concentrations in the pM range for all variants (while high nM concentrations were required using RBD-WT). Moreover, RBD-62 completely blocked viral entry and replication using at low nM concentrations (gray zone, FIG. 6D), while RBD-WT reduced viral load only by 2-3 orders of magnitude at the highest concentration (1 µM). No cytotoxicity was recorded for either for RBD-WT or RBD-62.

Overall, the results here clearly demonstrate that RBD-62 is a very powerful inhibitor of SARS-COV-2 infection on cells, with nM concentrations of the inhibitor completely blocking infection.

Example 4

Nebulizing RBD62 and Type I Interferon

Figure 7A:
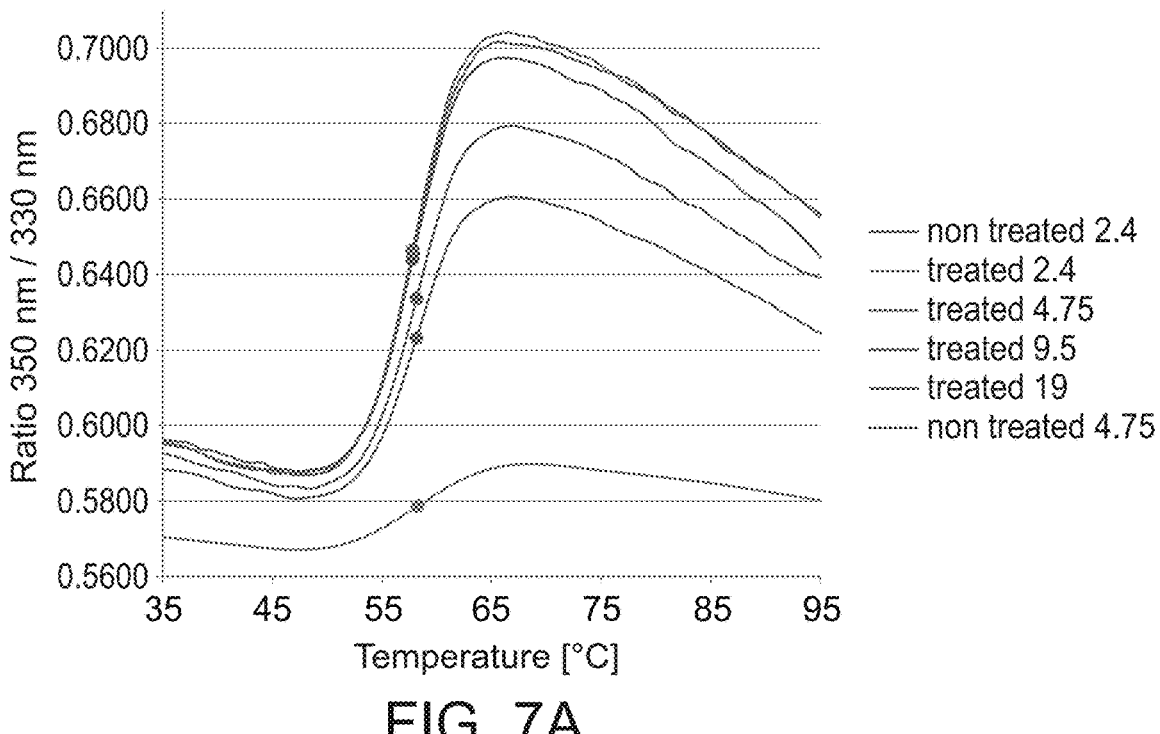
FIGS. 7A-C Protein quality control after nebulization. Protein quality was assessed using the Tycho N6, which shows melting curves (as observed from fluorescence ratio at 350 and 330 nm emission), from which the percent active protein can be calculated.
Figure 7B:
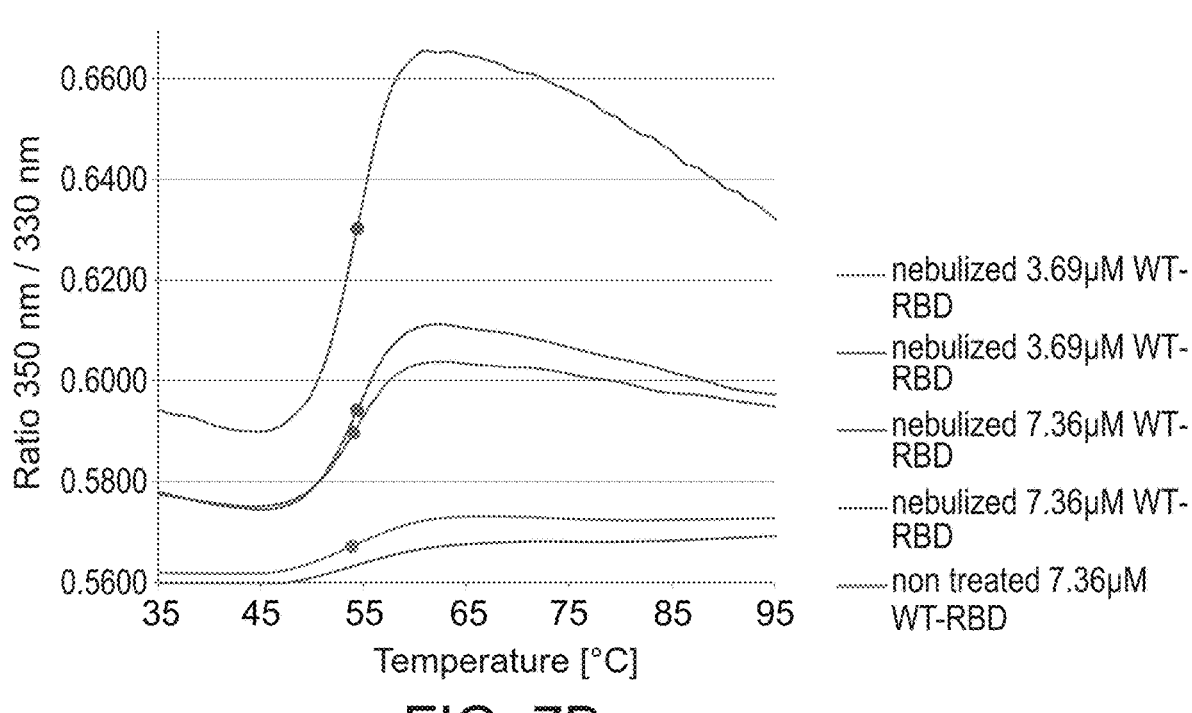

Proteins are difficult to nebulize, due to the shear stress that can cause protein unfolding and loss of biological activity. A vibrating mesh nebulizer (VMN, Acrogen Inc. the Acrogen® Solo) was used for to generate micrometer-sized droplets from a solution of the proteins. Protein recovery was determined by collecting the aerosolized protein in a 15 ml polypropylene tube directly following the nebulizer. The quality and amount of the recovered protein was measured using the Tycho™ NT.6 Nano-DSF (NanoTemper). The profile ratios for four concentrations (2.4-19 µM) of RBD62 treated by the Acrogen® Solo nebulizer show that the quantitatively RBD62 recovers at this concentration range. The profile is as expected and the temperature mid-point for unfolding (Tm) remains similar to the non-treated protein. Using the measured optical density (OD), the recovery of RBD62 was 98% at 19 µM, 84% for 9.5 µM, 75% for 4.76 µM and dropped to 45% for the 2.4 µM sample (FIG. 7A). In comparison, the recovery of the wild type RBD (WT-RBD) nebulized at 7.36 µM was 48% instead of the ~80% expected for RBD62 mutant at the same concentration (FIG. 7B). Thus, as expected by the elevated Tm of RBD62, it also provides increased stability as nebulized protein.

Figure 7C:
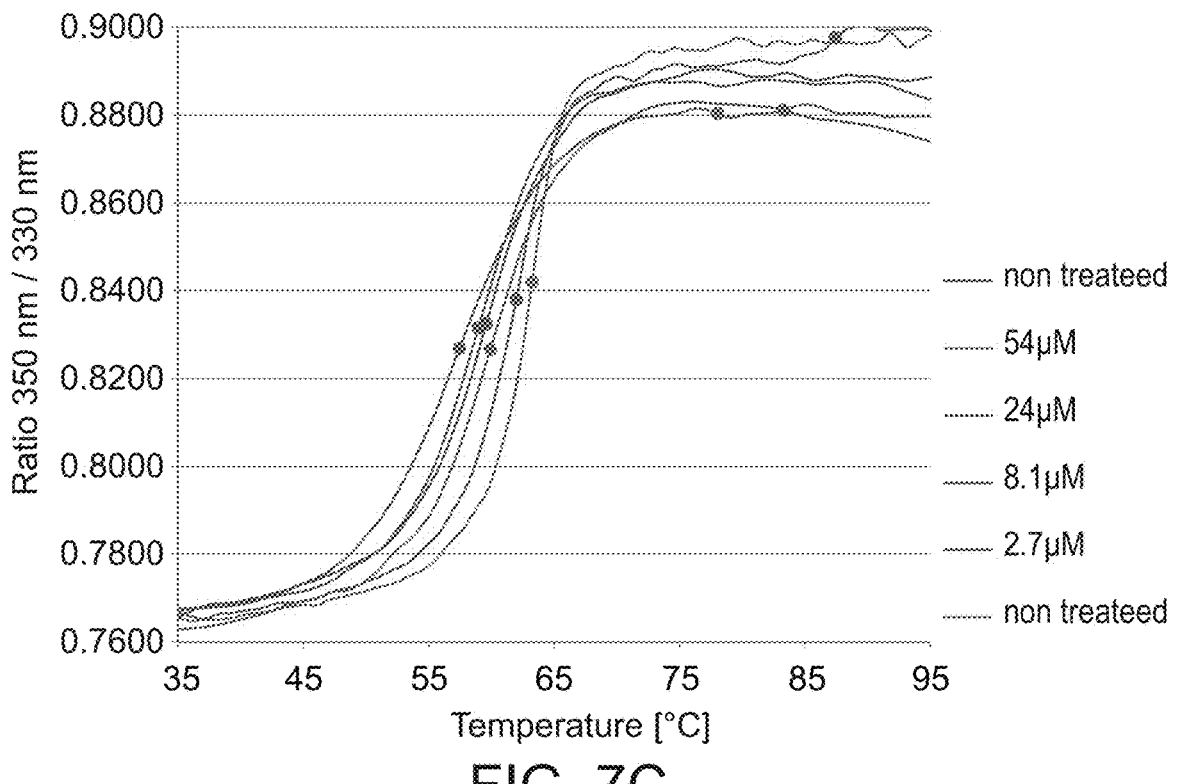

Interferon-α2 was nebulized as the RBD62 by an Acrogen® Solo nebulizer at four concentrations and the aerosol was collected as before directly into a 15 ml tube. 200 µl of IFN was nebulized at 2.7, 8.1, 24 and 54 µM in PBS. The quality and recovery of the IFNα2 after VMN was analyzed by Tycho™ NT.6. The chromatogram in FIG. 7C shows that at all tested concentrations there is native protein. Calculating the recovery of the treated IFNα from the brightness values (using a calibration curve, where the concentration (Y) of IFN-α2 at µg/ml $Y=2.4117X-14.506$, with X being the brightness value) shows that at initial protein concentration of 24 µM and above, the recovery is above 85%. At 8.1 µM the recovery is less than 60% and at 2.7 µM the recovery drops to 40%.

Figure 8:
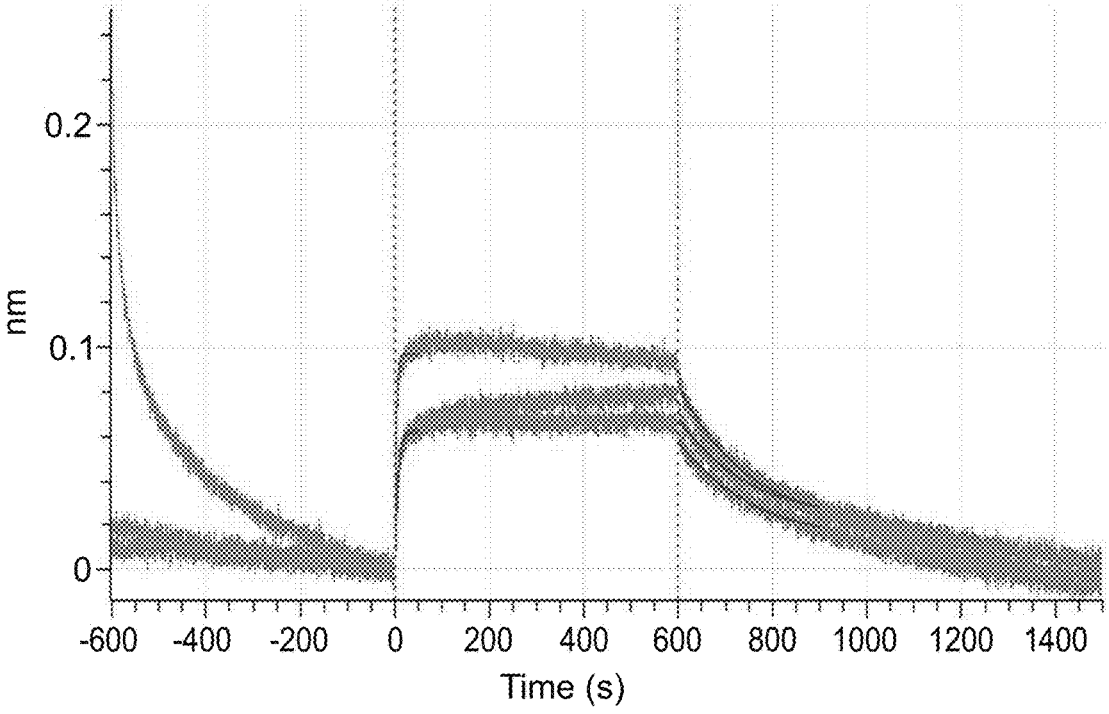
FIG. 8 is a graph illustrating the overlap results of Octet analysis of three chromatograms of IFN-α solutions. The chromatogram with the highest level of response is for non-treated, control protein at a concentration of 2.7 µM. The two other curves are of nebulized IFNα2, with and without RBD62, at protein concentrations of 1.1 µM (as determined using the Tycho instrument). The calculated rate constants for the three chromatograms is the same, suggesting that after nebulization Interferon-α retains its activity.

To further quantify the yield of active IFN-α2 following nebulization (with or without RBD-B62), the Octet RED96e of PALL ForteBio was used, which measures its binding to the IFN receptor IFNAR2. The receptor was immobilized through amine-coupling to a sensor surface, after it was immersed in solution collected after nebulization. FIG. 8 shows real-time association and dissociation of IFN α2 to IFNAR2, from which the rates of association and dissociation can be calculated. The dissociation rate constant ($k_d$) was calculated to be $0.006$ s$^{-1}$, independent of whether control or pre-nebulized IFNα2 was applied. The association rate constant ($k_a$) was calculated to be $3.4 \times 10^6$ M$^{-1}$ s$^{-1}$ for the non-treated sample (at a concentration of 2.7 αM), and $3.4$-$3.6 \times 10^6$ M$^{-1}$ s$^{-1}$ for the nebulized (in PBS) collected samples (nebulization was done using also 2.7 µM IFNα2). Nebulization was done in PBS, with or without 2.4 αM RBD62, resulting in the same $k_a$ value. Still, as measured using the Tycho instrument, the IFN α2 protein yield was only ~40% at this protein concentration.

To assess the biological activity of the nebulized proteins, cell cultures were grown on a 12 mm diameter insert designed for tissue culture (Corning Inc.), seeded a day before the experiment with $7$-$10 \times 10^4$ cells per insert. For nebulization treatment, the insert was placed at the bottom of a 50 ml falcon tube, with its top surface being open to air and its bottom immersed in 0.5 ml of medium. The volume of each protein sample solution was 200 µl per treatment.

Figure 9:
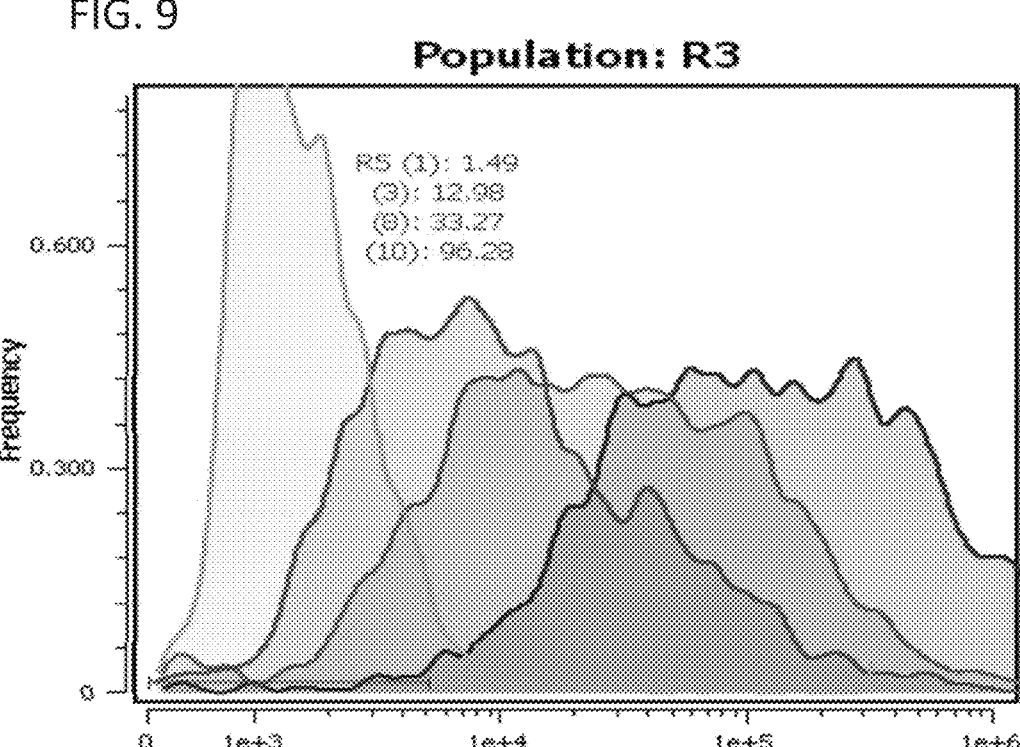
FIG. 9. show the FACS analysis of HEK cells treated with aerosols containing varying concentrations of RBD62. The higher the concentration—the higher the blocking efficiency. Samples order from high to low: Blue-cells treated by BSA only (mean, average from 2 experiments, $2.9 \times 10^5$), green treated with 0.235 µM B62 (mean=$1.1 \times 10^5$), pink-treated with 0.95 pM RBD62 (mean=$3.7 \times 10^4$) and orange-treated with 4.7 µM RBD62 (mean=$3.5 \times 10^3$). Each treatment vol-

A binding assay was developed for nebulized RBD6 by analyzing its ability to preferentially block binding of color-labeled WT-RBD to ACE2 on HEK293 cells overexpressing ACE2 (stable transgenic cell line GenScript Cat. No. M00770). Cells were seeded on Corning 12 mm inserts as described above. Following exposure to RBD62 aerosol, 125 µl medium containing WT-RBD labeled with Biotium Inc. CF-640R Succinimidyl Ester (Cat. #92108) were added to the cell medium. After 1 hour, the cells were removed from the insert by 5 mM EDTA solution in PBS, diluted and washed twice by PBS+0.5% BSA to remove toxic EDTA and unbound labeled WT-RBD. The cells were analyzed by flow cytometry to measure the difference in fluorescence intensity between cells treated with nebulized blank protein (0.5-2 mg/ml BSA) to cells treated with RBD-62 (1-20 µg/ml), thus testing whether RBD62 blocks the ACE2 receptors on the surface of the HEK-ACE2 cells. FIG. 9 illustrates dose-dependent results of the binding experiment. Samples order from high to low: Blue-cells treated by BSA only (mean, average from 2 experiments, $2.9 \times 10^5$), green treated with 0.235 µM B62 (mean=$1.1 \times 10^5$), pink-treated with 0.95 µM RBD62 (mean=$3.7 \times 10^4$) and orange-treated with 4.7 µM RBD62 (mean=$3.5 \times 10^3$). Each treatment volume was 200 µl on ~120,000 cells. The red numbers in the graphs represent the % of non-fluorescent cells: the first run at the top, the last run at the bottom.

To increase the efficacy of nebulized RBD62 and to increase its stability during the nebulization, the present inventors searched for superior formulations of the protein-containing solution. Gelatin (Sigma-Aldrich Cat. #G8150 or G1890) was found to have a strong positive effect on RBD62 stability upon nebulization. FIG. 10 shows results of a competition experiment against bound WT-RBD labeled with CF640. The control treatments are cells nebulized by BSA only (blue line). The experiment compares the activity of 2 µg in 0.2 ml PBS of RBD62 (violet) with addition of 0.4 or 2 mg/ml gelatin (orange) after nebulization in blocking the binding of labeled WT-RBD to the HEQ293-ACE2 cells. The results, shown in FIG. 10 and accompanied table, show up to 29-fold increase in the efficiency of RBD62 in blocking the ACE2 receptor in a formulations containing 2 mg/ml gelatin compared to samples without gelatin.

TABLE 6

| Treatment | | Popu. 642 | Count | % Gated | Mean 642-702/87 |
|---|---|---|---|---|---|
| BSA in 0.1 PBS | (1).R3 | 5494 | 92 | | 161362 |
| BSA in PBS | (2).R3 | 5667 | 94 | | 139424 |
| B62 in 0.5 PBS | (3).R3 | 5547 | 92 | | 65284 |
| B62 in 0.5 PBS | (4).R3 | 5616 | 94 | | 53904 |
| gelatin in 0.1 PBS | (5).R3 | 5771 | 89 | | 109840 |
| gelatin in PBS | (6).R3 | 5775 | 89 | | 162524 |
| gelatin in PBS | (7).R3 | 6092 | 94 | | 145402 |
| B62 + gelatin in 0.1 PBS | (8).R3 | 6029 | 93 | | 6278 |
| B62 + gelatin in 0.25 PBS | (9).R3 | 5619 | 86 | | 5467 |
| B62 + gelatin in 0.25 PBS | (10).R3 | 6719 | 90 | | 5110 |
| B62 + gelatin in 0.5 PBS | (11).R3 | 7016 | 94 | | 6860 |
| B62 + gelatin in PBS | (12).R3 | 6889 | 92 | | 7872 |

Droplet size distribution was measured with RBD62 in 0.5×BS with and without the addition of 1 or 2 mg/ml gelatin using the Aerogen® Solo VM nebulizer. Table 7 shows the size distribution and droplet number concentration of nebulized RBD62 (10 μg/ml) in 100% relative humidity. The main conclusions are:

1. In general, we did not observe significant differences between the three nebulized samples, tested for aerosol size distributions without a carrier gas. The geometric mean diameter (GMD) is 2.86±0.14 μm on average, and the mass concentration was 1.07±0.15 g m$^{-3}$.
2. With introducing 2 LPM air flow as carrier gas, aerosol mean size slightly decreased to 2.79±0.07 μm, and the mass concentration was 1.13±0.27 g m$^{-3}$. The shift in size is attributed to lower relative humidity while the increased mass concentration is attributed to lower wall loss or deposition in presence of carrier gas.
3. From the GMD, the nebulized aerosols (<3 μm) are in the correct size range to be efficiently inhaled into the lungs.

46

Biological activity of IFNα2 and IFNβ following nebulization was performed by monitoring STAT1 phosphorylation induced by nebulized interferon. STAT1 activation was studied in HeLa cells treated with nebulized IFNα2 and IFNβ (30 μg/ml+0.5 mg/ml gelatin) using fluorescent anti pSTAT1 (Tyr.701) monoclonal antibodies. As a negative control, a HeLa cell line with knock-out for both the interferon receptors (IFNAR1 and IFNAR2) treated with the same nebulized IFNα2 and IFNβ was used. FIG. 11 shows FACS results of the pSTAT1 activation assay following exposure to aerosolized IFNα2 and IFNβ on HeLa cells. The results clearly show that interferon retains its biological activity at this concentration.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

TABLE 7

| | Droplet size distribution after nebulization | | | | | |
|---|---|---|---|---|---|---|
| | Without air flow | | | 2.0 LPM air flow | | |
| Formulation | RBD-B62 | RBD-B62 + 1 mg/ml Gelatin | RBD-B62 + 2 mg/ml Gelatin | RBD-B62 | RBD-B62 + 1 mg/ml Gelatin | RBD-B62 + 2 mg/ml Gelatin |
| Median size (μm) | 3.27 ± 0.02 | 3.21 ± 0.04 | 2.96 ± 0.08 | 2.97 ± 0.19 | 2.78 ± 0.17 | 3.10 ± 0.12 |
| Mean size (μm) | 3.62 ± 0.03 | 3.58 ± 0.04 | 3.28 ± 0.08 | 3.47 ± 0.14 | 3.37 ± 0.13 | 3.43 ± 0.13 |
| GMD (μm) | 2.96 ± 0.03 | 2.92 ± 0.03 | 2.70 ± 0.06 | 2.80 ± 0.14 | 2.70 ± 0.11 | 2.84 ± 0.09 |
| Number Concentration (cm$^{-3}$) | (3.49 ± 0.04) × 10$^4$ | (3.45 ± 0.01) × 10$^4$ | (3.43 ± 0.03) × 10$^4$ | (3.45 ± 0.02) × 10$^4$ | (3.42 ± 0.02) × 10$^4$ | (3.42 ± 0.02) × 10$^4$ |
| Mass Concentration (mg m$^{-3}$) | (1.18 ± 0.05) × 10$^3$ | (1.14 ± 0.03) × 10$^3$ | (0.90 ± 0.05) × 10$^3$ | (1.15 ± 0.11) × 10$^3$ | (1.13 ± 0.08) × 10$^3$ | (1.10 ± 0.08) × 10$^3$ |

What is claimed is:

1. A polypeptide comprising an amino acid sequence of SARS COV-2 receptor-binding domain (RBD), wherein said amino acid sequence comprises a modification at position 358 and at least two additional modifications at two positions selected from the group consisting of 484, 498 and 501, wherein the numbering of the positions of the modifications is according to UniProtKB-P0DTC2 (SEQ ID NO: 37), wherein said polypeptide binds soluble, monomeric angiotensin-converting enzyme 2 (ACE2) receptor when expressed on the surface of yeast cells with at least 50 fold higher affinity than the wild-type RBD having an amino acid sequence as set forth in SEQ ID NO: 45, when assayed under identical conditions, wherein said polypeptide comprises at least 170 amino acids of said RBD.

2. The polypeptide of claim 1, comprising modifications at each of the positions 358, 484, 498 and 501, and optionally comprising a modification at position 460.

3. The polypeptide of claim 1, wherein said modification at position 358 comprises a I358F substitution, wherein said modification at position 484 comprises a E498K substitution, wherein said modification at position 498 comprises a Q498R substitution, or said modification at position 501 comprises a N501Y substitution.

4. The polypeptide of claim 2, comprising the substitutions:
   (i) I358F, N460K, E484K, S494P, Q498R and N501Y;
   (ii) I358F, N460K, E484K, Q498R and N501Y;
   (iii) I358F, E484K, Q498R and N501Y;
   (iv) I358F, V445K, N460K, I468T, T470M, S477N, E484K, Q498R and N501Y; or
   (v) I358F, V367W, R408D, K417V, V445K, N460K, I468T, T470M, S477N, E484K, Q498R and N501Y.

5. An isolated polypeptide comprising an amino acid sequence at least 99% identical to SEQ ID NO: 38, 39 or 40.

6. The isolated polypeptide of claim 1, comprising no more than 250 amino acids of the S1 subunit of the spike protein of SARS COV-2.

7. An isolated polynucleotide encoding the polypeptide of claim 1.

8. A dimer comprising two monomers linked by a linker, wherein each of said two monomers comprises an amino acid sequence encoding SARS-COV-2 receptor-binding domain (RBD), wherein each of said monomers binds soluble, monomeric angiotensin-converting enzyme 2 receptor when expressed on the surface of yeast cells with at least 50 fold higher affinity than the wild-type RBD having an amino acid sequence as set forth in SEQ ID NO: 45, when assayed under identical conditions, wherein each of said monomers comprises a modification at position 358, wherein the numbering of the position of the modification is according to UniProtKB-PODTC2 (SEQ ID NO: 37).

9. The dimer of claim 8, wherein the amino acid sequence of said two monomers is at least 99% identical to SEQ ID NO: 38, 39 or 40.

10. The dimer of claim 8, wherein a first of said two monomers comprises an amino acid sequence as set forth in SEQ ID NO: 39 and a second of said two monomers comprises an amino acid sequence as set forth in SEQ ID NO: 40.

11. An isolated polynucleotide, encoding the dimer of claim 8, wherein said linker is a peptide linker.

12. The isolated polynucleotide of claim 11, being an mRNA.

13. A vaccine comprising the isolated polypeptide of claim 1 or a polynucleotide encoding said polypeptide and an immunologically acceptable carrier.

14. The vaccine of claim 13, further comprising an adjuvant.

15. A pharmaceutical composition comprising as an active ingredient the isolated polypeptide of claim 1 or a polynucleotide encoding said polypeptide, and a pharmaceutically acceptable carrier.

16. The pharmaceutical composition of claim 15, being formulated for inhalation.

17. A method of treating a coronavirus infection in a subject in need thereof, comprising administering to the subject a therapeutically effective amount of the polypeptide of claim 1 or a polynucleotide encoding said polypeptide, thereby treating the coronavirus infection.

18. The method of claim 17, wherein said administering is effected by inhalation.

19. An article of manufacture comprising the polypeptide of claim 1, or a polynucleotide encoding said polypeptide and an anti-inflammatory agent.

* * * * *